(12) United States Patent
Addison et al.

(10) Patent No.: US 11,419,506 B2
(45) Date of Patent: Aug. 23, 2022

(54) SYSTEM AND METHOD FOR IDENTIFYING BLOOD PRESSURE ZONES DURING AUTOREGULATION MONITORING

(71) Applicant: COVIDIEN LP, Mansfield, MA (US)

(72) Inventors: Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 592 days.

(21) Appl. No.: 15/666,167

(22) Filed: Aug. 1, 2017

(65) Prior Publication Data
US 2018/0049649 A1 Feb. 22, 2018

Related U.S. Application Data

(60) Provisional application No. 62/378,026, filed on Aug. 22, 2016, provisional application No. 62/378,022, filed on Aug. 22, 2016.

(51) Int. Cl.
*A61B 5/00* (2006.01)
*A61B 5/021* (2006.01)
(Continued)

(52) U.S. Cl.
CPC .............. *A61B 5/021* (2013.01); *A61B 5/002* (2013.01); *A61B 5/14546* (2013.01);
(Continued)

(58) Field of Classification Search
CPC ... A61B 5/021; A61B 5/0205; A61B 5/02028; A61B 5/7239; G16H 50/20
See application file for complete search history.

(56) References Cited

U.S. PATENT DOCUMENTS 4,776,339 A 10/1988 Schreiber
5,351,685 A 10/1994 Potratz
(Continued)

FOREIGN PATENT DOCUMENTS

EP 615723 A1 9/1994
WO WO9843071 A1 10/1998
(Continued)

OTHER PUBLICATIONS

Addison, P. S., et al.; "Low-Oscillation Complex Wavelets," Journal of Sound and Vibration, 2002, vol. 254, Elsevier Science Ltd., pp. 1-30.
(Continued)

*Primary Examiner* — Allen Porter
*Assistant Examiner* — Michael A Catina
(74) *Attorney, Agent, or Firm* — Shumaker & Sieffert, P.A.

(57) ABSTRACT

A monitor configured to monitor autoregulation includes a memory encoding one or more processor-executable routines and a processor configured to access and execute the one or more routines encoded by the memory. When executed, the routines cause the processor to receive one or more physiological signals from a patient, determine a measure indicative of an autoregulation status of the patient based on the one or more physiological signals, generate an autoregulation alarm indicative of an impaired autoregulation status when the measure exceeds a predetermined threshold for more than a predetermined period of time.

19 Claims, 8 Drawing Sheets

(51) Int. Cl.
  *A61B 5/1455* (2006.01)
  *A61B 5/145* (2006.01)
  *A61B 5/0205* (2006.01)
  *A61B 5/026* (2006.01)

(52) U.S. Cl.
  CPC ........ *A61B 5/14552* (2013.01); *A61B 5/7246* (2013.01); *A61B 5/7267* (2013.01); *A61B 5/7278* (2013.01); *A61B 5/742* (2013.01); *A61B 5/7405* (2013.01); *A61B 5/746* (2013.01); *A61B 5/0205* (2013.01); *A61B 5/0261* (2013.01); *A61B 5/14553* (2013.01); *A61B 5/7445* (2013.01); *A61B 2505/03* (2013.01); *A61B 2505/07* (2013.01)

(56) References Cited

U.S. PATENT DOCUMENTS

| | | |
|---|---|---|
| 5,482,034 A | 1/1996 | Lewis et al. |
| 5,533,507 A | 7/1996 | Potratz |
| 5,577,500 A | 11/1996 | Potratz |
| 5,584,296 A | 12/1996 | Cui et al. |
| 5,626,140 A | 5/1997 | Feldman et al. |
| 5,803,910 A | 9/1998 | Potratz |
| 5,934,277 A | 8/1999 | Mortz |
| 6,385,471 B1 | 5/2002 | Mortz |
| 6,438,399 B1 | 8/2002 | Kurth |
| 6,453,183 B1 | 9/2002 | Walker |
| 6,505,060 B1 | 1/2003 | Norris |
| 6,510,329 B2 | 1/2003 | Heckel |
| 6,599,251 B2 | 7/2003 | Chen et al. |
| 6,668,182 B2 | 12/2003 | Hubelbank |
| 6,714,803 B1 | 3/2004 | Mortz |
| 6,754,516 B2 | 6/2004 | Mannheimer |
| 6,896,661 B2 | 5/2005 | Dekker |
| 6,987,994 B1 | 1/2006 | Mortz |
| 7,001,337 B2 | 2/2006 | Dekker |
| 7,221,969 B2 | 5/2007 | Stoddart et al. |
| 7,268,873 B2 | 9/2007 | Sevick-Muraca et al. |
| 7,744,541 B2 | 6/2010 | Baruch et al. |
| 8,556,811 B2 | 10/2013 | Brady |
| 2004/0097797 A1 | 5/2004 | Porges et al. |
| 2005/0004479 A1 | 1/2005 | Townsend et al. |
| 2005/0033129 A1 | 2/2005 | Edgar, Jr. et al. |
| 2005/0192488 A1 | 9/2005 | Bryenton et al. |
| 2005/0192493 A1 | 9/2005 | Wuori |
| 2007/0004977 A1 | 1/2007 | Norris |
| 2007/0049812 A1 | 3/2007 | Aoyagi et al. |
| 2008/0081974 A1 | 4/2008 | Pav |
| 2008/0146901 A1 | 6/2008 | Katura et al. |
| 2008/0200785 A1 | 8/2008 | Fortin |
| 2008/0228053 A1 | 9/2008 | Wang et al. |
| 2009/0326386 A1 | 12/2009 | Sethi et al. |
| 2010/0010322 A1 | 1/2010 | Brady |
| 2010/0030054 A1 | 2/2010 | Baruch et al. |
| 2010/0049082 A1 | 2/2010 | Hu et al. |
| 2011/0046459 A1 | 2/2011 | Zhang et al. |
| 2011/0105912 A1* | 5/2011 | Widman ............ A61B 5/02028 600/483 |
| 2012/0136605 A1 | 5/2012 | Addison et al. |
| 2012/0149994 A1 | 6/2012 | Luczyk et al. |
| 2012/0253211 A1 | 10/2012 | Brady et al. |
| 2012/0271130 A1 | 10/2012 | Benni |
| 2013/0190632 A1 | 7/2013 | Baruch et al. |
| 2014/0073888 A1 | 3/2014 | Sethi et al. |
| 2014/0275818 A1 | 9/2014 | Kassem et al. |
| 2014/0278285 A1 | 9/2014 | Marmarelis et al. |
| 2016/0106372 A1 | 4/2016 | Addison et al. |
| 2016/0324425 A1 | 11/2016 | Addison et al. |
| 2016/0345913 A1 | 12/2016 | Montgomery et al. |
| 2016/0367197 A1 | 12/2016 | Addison et al. |
| 2017/0000395 A1 | 1/2017 | Addison et al. |
| 2017/0000423 A1 | 1/2017 | Addison et al. |
| 2017/0095161 A1 | 4/2017 | Addison et al. |
| 2017/0105631 A1 | 4/2017 | Addison et al. |
| 2017/0105672 A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | 2010144961 A1 | 12/2010 |
| WO | WO2016182853 A1 | 11/2016 |

OTHER PUBLICATIONS

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," Shock, vol. 34, No. 5, pp. 455-460 (2010).

(56) References Cited

OTHER PUBLICATIONS

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.
Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.
Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.
Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).
Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," *Medical & Biological Engineering & Computing*, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).
Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.
Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics—the macro- vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

(56) References Cited

OTHER PUBLICATIONS

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," Neuro-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu, Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

Chuan et al., "Is cerebrovascular autoregulation associated with outcomes after major noncardiac surgery? A prospective observational pilot study," Acta Anaesthesiol Scand., Aug. 5, 2018, 10 pp.

International Search Report and Written Opinion of International Application No. PCT/US2017/045309, dated Nov. 3, 2017, 10 pp.

* cited by examiner

SYSTEM AND METHOD FOR IDENTIFYING BLOOD PRESSURE ZONES DURING AUTOREGULATION MONITORING

CROSS-REFERENCE TO RELATED APPLICATIONS

This application claims priority to and the benefit of Provisional Application No. 62/378,022, entitled "SYSTEM AND METHOD FOR PROVIDING AN ALARM DURING AUTOREGULATION MONITORING," filed Aug. 22, 2016, and Provisional Application No. 62/378,026, entitled "SYSTEM AND METHOD FOR IDENTIFYING BLOOD PRESSURE ZONES DURING AUTOREGULATION MONITORING," filed Aug. 22, 2016, which are herein incorporated by reference in their entirety for all purposes.

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. However, existing systems may not reliably determine the patient's autoregulation status and/or effectively provide an alarm indicative of the patient's autoregulation status.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
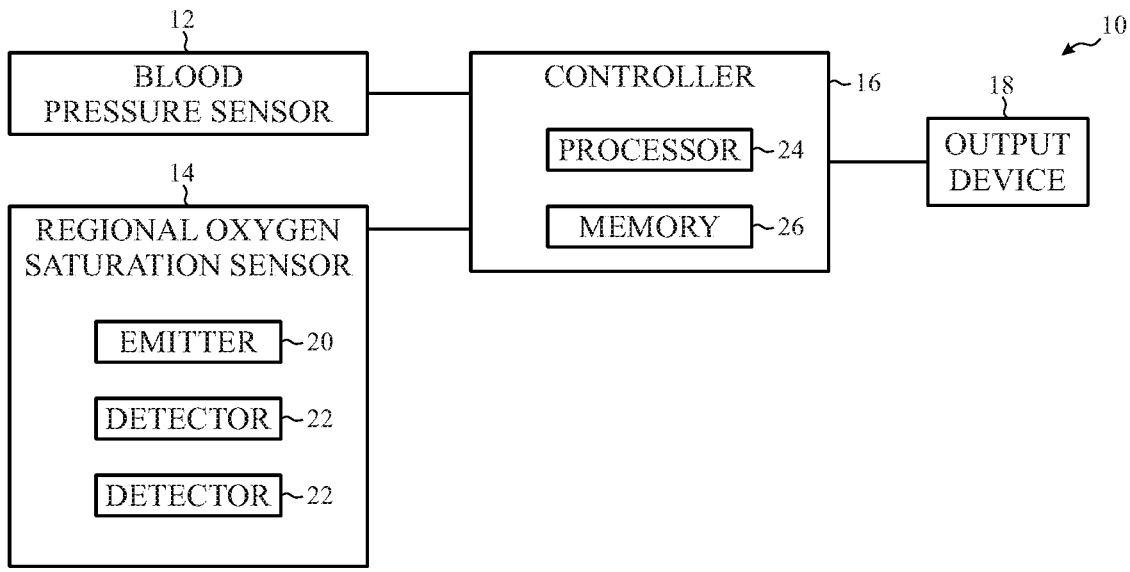
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a patient's autoregulation may be monitored via correlation-based measures (e.g., autoregulation indices) indicative of the patient's autoregulation status, such as a cerebral oximetry index (COx), a hemoglobin volume index (HVx), a mean velocity index (Mx), and/or a pressure reactivity index (PRx). Such correlation-based measures may be based on a correlation between the patient's blood pressure and a parameter indicative of blood flow. For example, as discussed in more detail below, COx values may be derived based on a linear correlation between the patient's blood pressure (e.g., arterial blood pressure) and oxygen saturation (e.g., regional oxygen saturation). A negative index value may indicate an intact autoregulation status across the corresponding blood pressure range, while a positive index value may indicate an impaired autoregulation status across the corresponding blood pressure range.

In some cases, a patient's autoregulation may be monitored based on non-correlation-based measures, such as respective gradients of a blood pressure signal and an oxygen saturation signal over a period of time. For example, a blood pressure gradient and an oxygen saturation gradient that trend together (e.g., change in the same direction) over the period of time may indicate an impaired autoregulation status across the corresponding blood pressure range. However, a blood pressure gradient and an oxygen saturation gradient that do not trend together (e.g., do not change in the same direction) over the period of time, may indicate an intact autoregulation status across the corresponding blood pressure range.

As discussed in more detail below, the disclosed systems and methods may use any suitable measure (e.g., COx, HVx, Mx, PRx, gradients) or combination of measures to monitor the patient's autoregulation and may be configured to generate an alarm indicative of the patient's autoregulation status. In some embodiments, the systems and methods may be configured to provide multiple alarms, such as a first alarm (e.g., blood pressure alarm or physiological parameter alarm) in response to changes in blood pressure and/or the parameter indicative of blood flow (e.g., oxygen saturation) and a second alarm (e.g., autoregulation alarm) in response to determination of an impaired autoregulation status. Such a configuration may provide a first notification to an operator that the patient's physiological parameter(s) has changed significantly and/or is outside of an acceptable blood pressure range, and also that the patient's blood pressure may have transitioned to a blood pressure at which the patient's autoregulation system does not function properly, and this configuration may further provide a second notification to the operator that the patient's autoregulation system is indeed impaired after sufficient data points are obtained to enable determination of the patient's autoregulation status (e.g., via calculation of a measure, such as COx, HVx, Mx, PRx, and/or gradients).

In some embodiments, the autoregulation alarm may be provided only if the patient's autoregulation system is impaired for more than a predetermined period of time. For example, the autoregulation alarm may be provided only after the measure exceeds a predetermined threshold for the predetermined period of time. In some embodiments, the autoregulation alarm may include multiple flags and/or alarms. For example, in some embodiments, an autoregulation flag (e.g., a first autoregulation alarm or indicator) may be set or provided upon an initial determination that the patient's autoregulation system is impaired (e.g., upon an initial detection of trending and/or a correlation between blood pressure and oxygen saturation, upon collection of a minimum number of data points to calculate a COx value with a first confidence level, etc.), and an autoregulation alarm (e.g., a second autoregulation alarm or indicator) may be provided if the patient's autoregulation system is impaired for more than a predetermined period of time (e.g., based on COx values over time and/or once sufficient data points are collected to determine the autoregulation status with a second confidence level).

A patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired.

Accordingly, in some embodiments, the systems and methods may be configured to access, utilize, and/or determine autoregulation limits, such as an upper limit of autoregulation (ULA) value and/or a lower limit of autoregulation (LLA) that approximately define an upper and a lower blood pressure (e.g., mean arterial pressure or MAP) boundary, respectively, within which autoregulation is generally intact and functioning properly (e.g., a blood pressure safe zone). Likewise, blood pressures approximately above the ULA and/or approximately below the LLA may be associated with impaired autoregulation function. The ULA and/or the LLA may be determined based on the measures indicative of autoregulation status (e.g., COx values) across various blood pressures as the patient's blood pressure and autoregulation status are monitored during a monitoring session. In some such embodiments, when the ULA and/or the LLA are known, the systems and methods may be configured to provide an alarm (e.g., an autoregulation alarm or an autoregulation limit alarm) indicative of the patient's autoregulation status based on an integral over time of a difference between the blood pressure and the ULA or the LLA. For example, the patient's blood pressure may fall below the LLA over a period of time, and the autoregulation alarm may be provided once the integral over time of the difference between the blood pressure and the LLA exceeds a predetermined integral threshold. Such a configuration may efficiently provide an alarm indicative of the patient's autoregulation status (e.g., as compared to providing an alarm based on a calculated measure, such as COx, HVx, Mx, PRx, or gradients), while also reducing nuisance alarms (e.g., as compared to providing an alarm each time the patient's blood pressure falls below the LLA or exceeds the ULA). In certain embodiments, the alarm(s) disclosed herein may include an audible indication via a speaker and/or a visual indication via a display.

As discussed in more detail below, embodiments disclosed herein may also be utilized to generate an autoregulation profile that indicates autoregulation zones indicative of a patient's blood pressure dependent autoregulation status. To facilitate discussion, certain examples provided herein relate to COx values. However, it should be understood that any suitable measure of autoregulation status may be utilized to monitor autoregulation, generate the autoregulation profile, determine the ULA and/or the LLA, and/or to generate an alarm. For example, HVx, Mx, PRx, and/or respective gradients of a blood pressure signal and an oxygen saturation signal may be utilized to monitor autoregulation, determine the ULA and/or the LLA, and/or to generate an alarm. Furthermore, HVx, Mx, PRx, and/or respective gradients of a blood pressure signal and an oxygen saturation signal may be used to determine whether the patient's autoregulation state is impaired or intact at a particular blood pressure, autoregulation state values may be assigned based on the determination of the autoregulation state, and the autoregulation profile may be generated and the corresponding indications provided in the manner set forth below.

FIG. 1 is a block diagram of an embodiment of a system 10 for monitoring autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., mean arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable determination of the patient's autoregulation status, to provide appropriate alarm(s), and/or to enable identification of autoregulation zone(s).

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. The emitter 20 may be driven to emit light by light drive circuitry of a monitor (e.g., a specialized monitor having a controller configured to control the light drive circuitry). In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm.

One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status and/or generation of an alarm. While the depicted oxygen saturation sensor 14 is a regional saturation sensor, the sensor 14 may be a pulse oximeter configured to obtain the patient's oxygen saturation or may be any suitable sensor configured to provide a signal indicative of the patient's blood flow. For example, the sensor 14 may be configured to emit light at a single wavelength (e.g., an isobestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to determine the patient's autoregulation status and/or to generate appropriate alarm(s). Additionally or alternatively, the controller 16 may be configured to process the blood pressure signal and the oxygen saturation signal to generate the autoregulation profile. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

The system 10 having the blood pressure sensor 12 and the oxygen saturation sensor 14 may be used to monitor the patient's autoregulation, generate alarms, and/or generate an autoregulation profile based on COx values or based on other appropriate measures, such as a relationship between a blood pressure gradient and an oxygen saturation gradient. It should be appreciated that the system 10 may be adapted (e.g., include other types of sensors) to monitor the patient's autoregulation, generate alarms, and/or generate an autoregulation profile based on other measures, such as HVx, Mx, PRx, or the like.

In some embodiments, the controller 16 may be configured to determine a cerebral oximetry index (COx) based on the blood pressure signal and the oxygen saturation signal. The COx is indicative of vascular reactivity, which is related to cerebral blood vessels' ability to control proper blood flow, via vasoconstriction (a narrowing of the blood vessel) and/or vasodilation (expansion of the blood vessel), for example. Thus, the COx is also indicative of whether the patient's autoregulation is impaired. The controller 16 may derive the COx by determining a linear correlation between blood pressure measurements and oxygen saturation measurements. The linear correlation may be based on a Pearson coefficient, for example. The Pearson coefficient may be defined as the covariance of the measured blood pressure (e.g., arterial blood pressure) and oxygen saturation divided by the product of their standard deviations. The result of the linear correlation may be a regression line between oxygen saturation measurements and blood pressure measurements, and the slope of the regression line may be indicative of the patient's autoregulation status. In one implementation, a regression line with a relatively flat or negative slope (e.g., regional oxygen saturation remains the same or decreases after blood pressure increases) may suggest that cerebral autoregulation is working properly, while a regression line with a positive slope (e.g., regional oxygen saturation increases after blood pressure increases) may suggest that the cerebral autoregulation is impaired.

Figure 2:
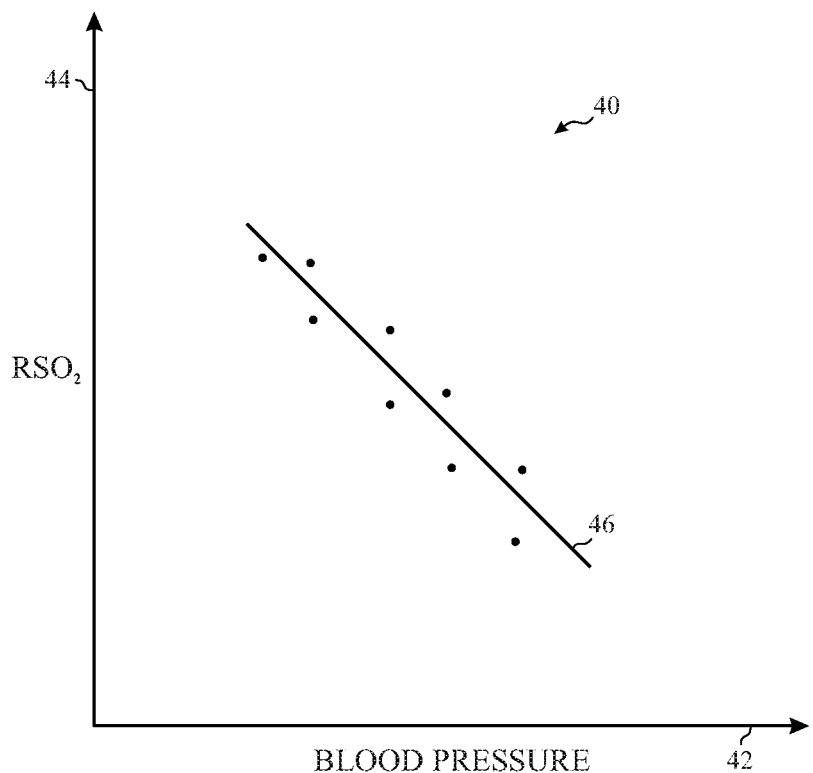
FIG. 2 is an example of a graph illustrating a linear correlation between oxygen saturation values and blood pressure values.

With the foregoing in mind, FIG. 2 is an example of a graph 40 illustrating a linear correlation between blood pressure measurements 42 (e.g., arterial blood pressure measurements) and oxygen saturation measurements 44. The result of the linear correlation may be a regression line 46 between the blood pressure measurements 42 and the oxygen saturation measurements 44, and the slope of the regression line 46 may be indicative of the patient's autoregulation status. In the illustrated example, the slope of the regression line 46 is negative and, thus, the COx value is between −1 and 0, which as discussed above, may indicate proper autoregulation. In such cases, the controller 16 may determine that the patient's cerebral autoregulation is functioning properly and may generate and/or output an appropriate signal indicative of the patient's autoregulation status to the output device 18, for example. However, when the regression line 46 has a positive slope and the COx value is between 0 and 1, or above some predetermined threshold between 0 and 1 (e.g., 0.1, 0.2, 0.3, 0.4, 0.5, 0.6, 0.7, 0.8, or 0.9), the controller 16 may determine that the patient's autoregulation is impaired and may generate and/or output the appropriate alarm(s). Accordingly, the controller 16 may be configured to determine the COx value and/or the patient's autoregulation status based on the linear correlation between the blood pressure measurements and oxygen saturation measurements obtained by the blood pressure sensor 12 and the oxygen saturation sensor 14, respectively.

Returning to FIG. 1, in the illustrated embodiment, the controller 16 includes a processor 24 and a memory device 26. The controller 16 may also include one or more storage devices. As discussed in more detail below, the processor 24 may be used to execute code stored in the memory device 26 or other suitable computer-readable storage medium or memory circuitry, such as code for implementing various monitoring functionalities. The processor 24 may be used to execute software, such as software for carrying out any of the techniques disclosed herein, such as processing the blood pressure signals and/or oxygen saturation signals, determining a measure of autoregulation (e.g., index value or gradients), determining the autoregulation status or state, identifying the LLA and/or the ULA, generating alarms, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for processing the blood pressure signals and/or oxygen saturation signals, determining a measure of autoregulation, determining the autoregulation status, identifying the LLA and/or the ULA, generating alarms, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the index value, the LLA, the ULA, predetermined thresholds, etc.), instructions (e.g., software or firmware for processing the blood pressure signals and/or oxygen saturation signals, determining a measure of autoregulation, determining the autoregulation status, identifying the LLA and/or the ULA, generating alarms, and so forth), predetermined thresholds, and any other suitable data.

As shown, the system 10 includes the output device 18. In some embodiments, the controller 16 may be configured to instruct the output device 18 to provide an alarm(s). In some embodiments, the alarm(s) may include audible alarms provided via a speaker of the output device 18 and/or visual indications provided via a display or a light of the output device 18, for example. The audible alarms may include spoken messages, beeps, or other sounds, which may differ in tones, durations, volume, tunes, or other types of audible features, based on the type of alarm and/or the severity of the alarm, for example. The visual indications may include text messages, colored displays, colored lights, or other types of visible features. The output device 18 may include any device configured to receive signals (e.g., signals indicative of the alarm(s), autoregulation status, the LLA, the ULA, the predetermined thresholds, the current blood pressure, the current oxygen saturation, or the like) from the controller 16 and visually and/or audibly output the alarm(s) and/or other information related to the patient's autoregulation status. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a specialized computer or monitor for patient monitoring).

Typical systems and methods for monitoring autoregulation may not efficiently provide an alarm indicative of an impaired autoregulation status. For example, some typical systems may obtain blood pressure and oxygen saturation data points over an extended period of time, such as 5 minutes or more, then calculate the COx value based on the data points, and subsequently provide an alarm if the COx value indicates impaired autoregulation. Advantageously, certain embodiments of the present disclosure include the controller 16 that is configured to efficiently provide one or more indications (e.g., alarms) indicative of the patient's autoregulation status. In certain embodiments, the controller 16 may be configured to provide a physiological parameter alarm (e.g., blood pressure alarm) in response to a change in blood pressure and/or a change in the parameter indicative of blood flow (e.g., oxygen saturation). For example, the physiological parameter alarm may be provided when the blood pressure and/or the oxygen saturation move outside of respective ranges, fall below respective lower thresholds, exceed respective upper thresholds, or the like. The controller 16 may additionally or alternatively be configured to provide an autoregulation alarm in response to determination of impaired autoregulation status. For example, the autoregulation alarm may be provided based on the COx value, or other suitable measure indicative of autoregulation status. Together, the physiological parameter alarm may quickly alert the operator to substantial changes in blood pressure and/or oxygen saturation to facilitate immediate treatment and to provide an early indicator of possible autoregulation system impairment, and the autoregulation alarm may alert the operator that the patient's autoregulation system is not functioning properly.

Figure 3A:
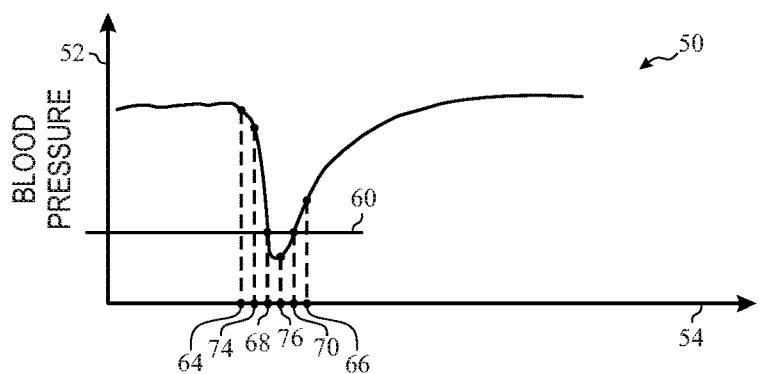
FIG. 3A is an example of a graph illustrating blood pressure over a period of time.
Figure 3B:
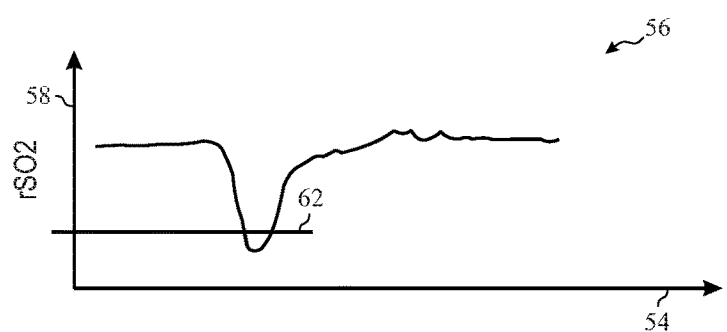
FIG. 3B is an example of a graph illustrating oxygen saturation over the period of time shown in FIG. 3A.

With the foregoing in mind, FIG. 3A is an example of a graph 50 illustrating blood pressure 52 over a period of time 54, and FIG. 3B is an example of a graph 56 illustrating oxygen saturation 58 over the period of time 54 shown in FIG. 3A. In some embodiments, the controller 16 may be configured to provide the physiological parameter alarm when the blood pressure 52 and/or the oxygen saturation 58 change substantially and/or fall outside of respective predetermined ranges. For example, with reference to FIG. 3A, the controller 16 may provide the physiological parameter alarm when the blood pressure 52 falls below a predetermined lower threshold 60. In certain embodiments, the controller 16 may provide the physiological parameter alarm only when both the blood pressure 52 is below the predetermined lower threshold 60 and the oxygen saturation 58 is below a predetermined lower threshold 62. In such cases, the physiological parameter alarm may provide an indication that the patient's blood pressure 52 and/or oxygen saturation 58 is outside of a respective acceptable range and requires attention and/or treatment. Because the patient's autoregulation system may not work properly at blood pressures outside of an intermediate range and/or because trending and/or correlation between the blood pressure 52 and the oxygen saturation 58 may be indicative of impaired autoregulation, the physiological parameter alarm may also provide an early indication that the patient's autoregulation system is potentially impaired.

Although FIGS. 3A and 3B show predetermined lower thresholds 60, 62 to facilitate discussion, it should be understood that the controller 16 may be configured to provide the physiological parameter alarm when the blood pressure 52 and/or the oxygen saturation 58 change by any certain amount and/or fall outside of any of a variety of respective suitable predetermined ranges. For example, the controller 16 may be configured to provide the physiological parameter alarm when the blood pressure 52 and/or the oxygen saturation 58 change by more than about 5, 10, 15, 20, or 25 percent over a period of time, such as less than 10, 15, 30, 60, 120, or 180 seconds. In some embodiments, the controller 16 may be configured to provide the physiological parameter alarm when the blood pressure 52 is outside of a predetermined range, such as about 50 to 130, 60 to 120, 70 to 110 mmHg, when the blood pressure 52 exceeds a predetermined upper threshold, such as about 110, 120, or 130 mmHg, and/or falls below a predetermined lower threshold, such as about 50, 60, or 70 mmHg. In some embodiments, the controller 16 may be configured to provide the physiological parameter alarm when the oxygen saturation 58 is outside of a predetermined range, such as about 50 to 100, 60 to 90, or 70 to 80 percent, when the oxygen saturation 58 exceeds a predetermined upper threshold, such as about 80, 90, or 100 percent, and/or falls below a predetermined lower threshold, such as about 50, 60, or 70 percent.

Additionally or alternatively, in some embodiments, the controller 16 may be configured to provide the autoregulation alarm indicative of an impaired autoregulation status. In some embodiments, the controller 16 may provide the autoregulation alarm after sufficient data points are obtained to enable determination of the patient's autoregulation status (e.g., via calculation of a measure, such as COx, HVx, Mx, PRx, or gradients). For example, the controller 16 may provide the autoregulation alarm after calculating a COx value based on data points obtained over a time window, such as approximately 0.5, 1, 3, or 5 minutes. In some embodiments, the controller 16 may provide the autoregulation alarm after obtaining a predetermined number of data points and/or once the measure (e.g., COx value) has a certain reliability (e.g., confidence level). For example, with reference to FIGS. 3A and 3B, the controller 16 may obtain sufficient data points between a first time 64 and a second time 66 to reliably calculate the COx value. In some such cases, the controller 16 may provide the physiological parameter alarm at a third time 68 when both the patient's blood pressure 52 and/or oxygen saturation 58 fall below respective thresholds 60, 62 and may provide the autoregulation alarm at the second time 66 if the COx value indicates that the patient's autoregulation system is impaired. When the patient's blood pressure 52 and/or oxygen saturation 58 move above the respective lower predetermined thresholds 60, 62 at a fourth time 70, the physiological parameter alarm may be deactivated. However, the autoregulation alarm may be provided until the controller 16 determines that the patient's autoregulation system is functioning properly, such as based on COx values over a subsequent time window.

In certain embodiments, the predetermined period of time over which the data points are collected to calculate the COx value, the number of data points used to calculate the COx value, and/or the confidence level thresholds for the COx value may be adjusted based on various factors. For example, the predetermined period of time over which the data points are collected to calculate the COx value prior to providing the autoregulation alarm may be greater if the physiological parameter alarm is active as compared to if the physiological parameter alarm is not active. In such cases, the physiological parameter alarm provides an alert to the operator to take corrective action with respect to the patient's blood pressure and provides an indication that the patient's autoregulation system may be impaired. Thus, it may be acceptable to increase the predetermined period of time in order to obtain more data points and determine an autoregulation status with a higher confidence level because the operator already has an indication of a physiological problem. However, in some embodiments, the predetermined period of time over which the data points are collected to calculate the COx value may be less if the physiological parameter alarm is active as compared to if the physiological parameter alarm is not active. For example, in some such cases, it may be desirable to reduce the predetermined period of time in order to more quickly provide the autoregulation alarm due to the patient's unstable condition.

In certain embodiments, the autoregulation alarm may be provided only after the controller 16 determines that the patient's autoregulation system is impaired for more than a predetermined period of time, such as longer than approximately 1, 3, 5, 10, or 15 minutes. For example, the autoregulation alarm may be provided only after the COx value exceeds a predetermined threshold (e.g., 0.1, 0.2, 0.3, 0.4, 0.5, 0.6, 0.7, 0.8, or 0.9) for more than the predetermined period of time. In some embodiments, the autoregulation alarm may include multiple flags and/or alarms. For example, in some embodiments, an autoregulation flag (e.g., a first autoregulation alarm or indicator) may be set or provided upon an initial determination that the patient's autoregulation system is impaired (e.g., upon an initial detection of a trend or correlation between blood pressure and oxygen saturation, upon collection of a minimum number of data points to calculate a COx value, upon collection of a number of data points to calculate a COx value with a first confidence level, etc.), and an autoregulation alarm (e.g., a second autoregulation alarm or indicator) may be provided if the patient's autoregulation system is impaired for more than a predetermined period of time (e.g., based on COx values over time, such as longer than approximately 1, 3, 5, 10, or 15 minutes). For example, with reference to FIGS. 3A and 3B, the autoregulation flag may be set at a fifth time 74 upon initial detection of a correlation between blood pressure 52 and oxygen saturation 58 (e.g., based on a COx value between 0 and 1, or above a threshold between 0 and 1, and/or having a first confidence level). At a time after the fifth time 74, such as at a sixth time 76, the controller 16 may provide the autoregulation alarm upon determination (e.g., based on a COx value based at least in part on data points obtained between the fifth time 74 and the sixth time 76) that the patient's autoregulation system is still impaired (e.g., has been impaired at least from the fifth time 74 to the sixth time 76). Such a configuration may provide an early indication of low blood pressure, low oxygen saturation, and/or possible impaired autoregulation (e.g., upon providing the physiological parameter alarm at the third time 68), as well as an early indication of autoregulation impairment (e.g., upon setting the autoregulation flag at the fifth time 74) and/or a confirmation of autoregulation impairment or an indication of extended autoregulation impairment (e.g., upon providing the autoregulation alarm at the sixth time 76). The relative times, number of data points utilized, and/or confidence level thresholds for setting the autoregulation flag and/or the autoregulation alarm may vary based on other factors, such as whether the first alarm is active or has been recently active (e.g., within 0.5, 1, 2, 3, 4, or 5 minutes). It should be understood that in certain embodiments, the controller 16 may be configured to provide an indication of intact autoregulation (e.g., based on the COx values).

Figure 4A:
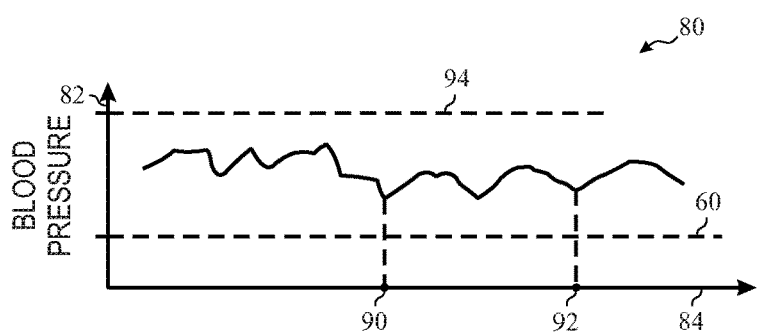
FIG. 4A is an example of a graph illustrating blood pressure over a period of time.
Figure 4B:
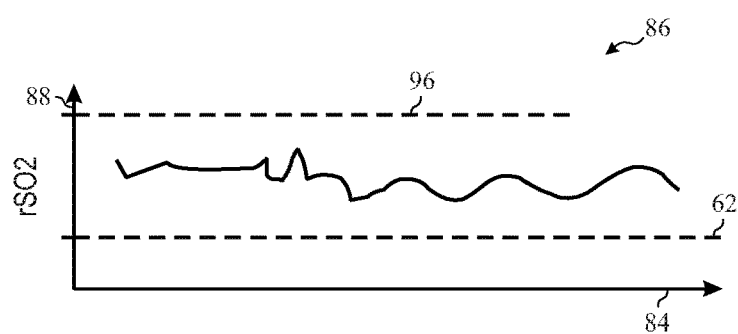
FIG. 4B is an example of a graph illustrating oxygen saturation over the period of time shown in FIG. 4A.

The above-described alarm systems and methods may be particularly useful in a clinical situation in which the patient's blood pressure 52 and oxygen saturation 58 drop significantly, as shown in FIGS. 3A and 3B. The above-described alarm systems and methods may also be particularly useful in a clinical situation in which the patient's blood pressure is narrowly below a lower limit of autoregulation (LLA) or narrowly above an upper limit of autoregulation (ULA). For example, FIG. 4A is an example of a graph 80 illustrating blood pressure 82 over a period of time 84, and FIG. 4B is an example of a graph 86 illustrating oxygen saturation 88 over the period of time 84. In FIGS. 4A and 4B, the blood pressure 82 and the oxygen saturation 88 are within acceptable predetermined respective ranges (e.g., above the lower thresholds 60, 62 and below the upper threshold 94, 96), and thus, the physiological parameter alarm may not be provided; however, at a first time 90, the blood pressure 82 drops to a level at which the patient's autoregulation system becomes impaired (e.g., below the LLA). As discussed above, in some embodiments, the autoregulation alarm may be provided if the controller 16 determines (e.g., based on a COx value) that the patient's autoregulation system is impaired for more than a predetermined period of time, such as equal to or longer than approximately 1, 3, 5, 10, or 15 minutes. In some embodiments, the controller 16 may provide the autoregulation flag upon initial detection of a correlation (e.g., at the first time 90), and then the controller 16 may provide the autoregulation alarm if the patient's autoregulation system is impaired for more than a predetermined period of time (e.g., based on COx values over time), such as at a second time 92.

As discussed above, a patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. Accordingly, in some embodiments, the systems and methods may be configured to receive an input indicative of or to determine the ULA and/or the LLA that approximately define an upper and a lower blood pressure (e.g., mean arterial pressure or MAP) boundary, respectively, within which autoregulation is generally intact and functioning properly.

Figure 5:
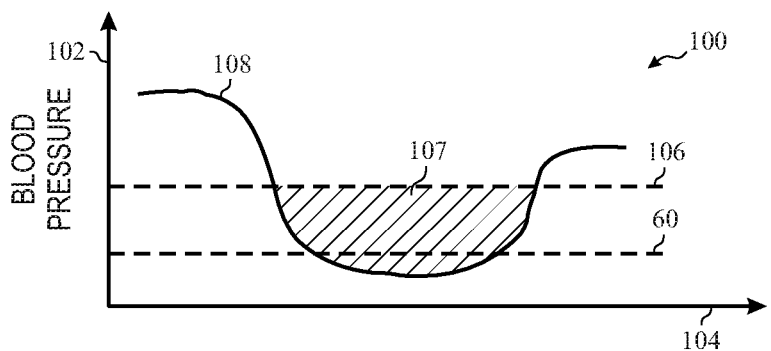
FIG. 5 is an example of a graph illustrating blood pressure over time and a lower limit of autoregulation (LLA)

With the foregoing in mind, FIG. 5 is an example of a graph 100 illustrating blood pressure 102 over time 104 and a lower limit of autoregulation (LLA) 106. In some embodiments, the LLA 106 may be determined during a monitoring session by calculating autoregulation measures (e.g., COx values) across blood pressures, or via any other suitable technique. Once the LLA 106 is known, the LLA 106 may then be utilized to provide an autoregulation limit alarm. For example, the controller 16 may provide the autoregulation limit alarm when the blood pressure 102 falls below the LLA 106. Additionally or alternatively, in some embodiments, the controller 16 may be configured to provide the autoregulation limit alarm when the blood pressure 102 falls below the LLA 106 for a more than a predetermined period of time. In some such cases, the controller 16 may be configured to calculate an integral over time of a difference between the blood pressure signal 108 and the LLA 106 (e.g., illustrated by the shaded area 107 in FIG. 5) and to provide the autoregulation alarm when the integral over time exceeds a predetermined integral threshold. The LLA 106 is shown to facilitate discussion, but it should be understood that the autoregulation alarm may be provided based on an integral over time of the difference between the blood pressure signal 108 and the ULA.

In some embodiments, the autoregulation limit alarm based on the integral over time may be combined with the physiological parameter alarm that is activated when the blood pressure 102 falls below the lower predetermined threshold 60. For example, the controller 16 may be configured to provide the physiological parameter alarm when the blood pressure and/or the oxygen saturation fall below respective lower predetermined thresholds 60, 62, as discussed above with respect to FIGS. 3A and 3B, and to provide the autoregulation limit alarm when the integral over time of the difference between the blood pressure 102 and the LLA 106 exceeds the predetermined integral threshold. In some embodiments, once the LLA 106 is known, the lower predetermined threshold 60 for blood pressure may be set to the LLA 106. In some such cases, the physiological parameter alarm may be provided when the blood pressure 102 falls below the LLA 106, and the autoregulation limit alarm may be provided when the integral over time of the difference between the blood pressure 102 and the LLA 106 exceeds the predetermined integral threshold. Such a configuration may provide a first alarm indicative of blood pressure associated with impaired autoregulation status and a second alarm indicative of an extended period of impaired autoregulation status.

In some embodiments, the alarm techniques may vary during different portions of the monitoring session. For example, during an initial period of a monitoring session and/or prior to determination of the LLA and/or the ULA, the controller 16 may be configured to provide the physiological parameter alarm when the blood pressure and/or oxygen saturation is outside of a respective acceptable range and to provide the autoregulation alarm in response to determination of an impaired autoregulation status based on the autoregulation measure (e.g., COx value), in the manner discussed above with respect to FIGS. 3A, 3B, 4A, and 4B. In some such embodiments, after determination of the LLA and/or the ULA, the controller 16 may be configured to provide the autoregulation limit alarm when an integral over time of the difference between the blood pressure signal 108 and the LLA 106 (or the blood pressure signal 108 and the ULA) exceeds the predetermined integral threshold. In some such embodiments, after determination of the LLA and/or the ULA, the controller 16 may adjust the thresholds for the physiological parameter alarm to the LLA and/or the ULA.

Figure 6:
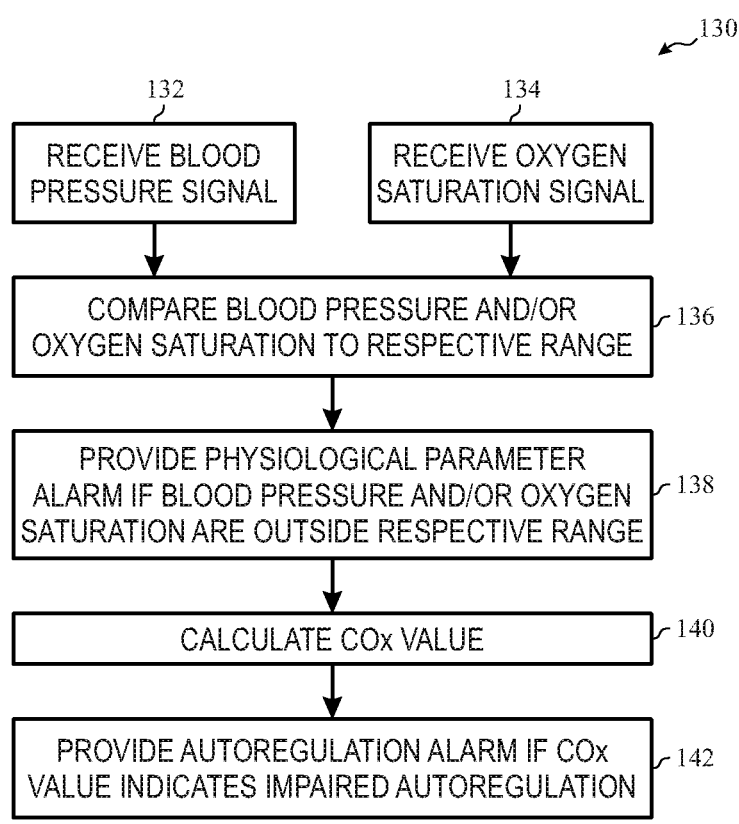
FIG. 6 is a process flow diagram of a method of providing an alarm during autoregulation monitoring, in accordance with an embodiment.
Figure 7:
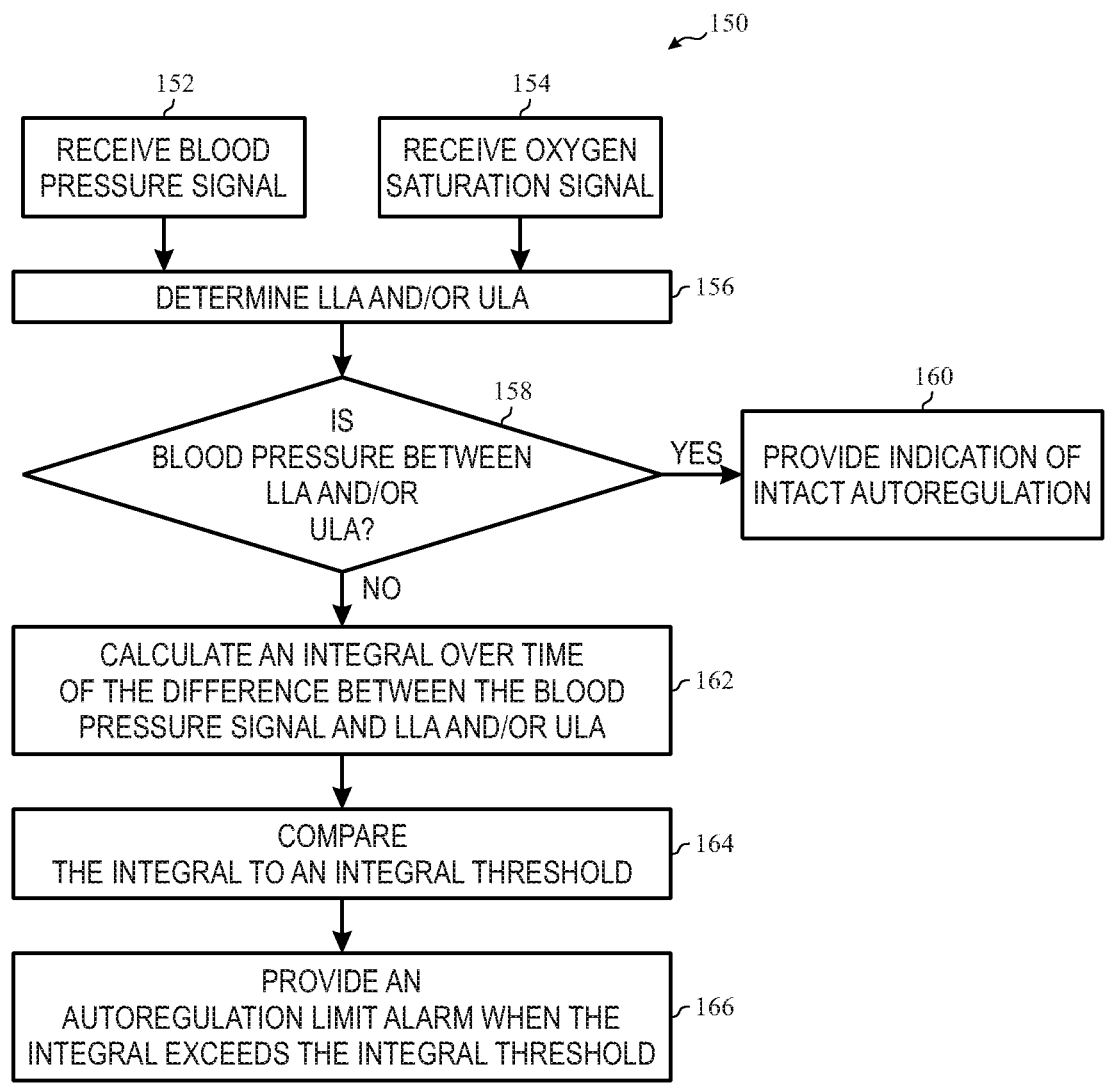
FIG. 7 is a process flow diagram of another method of providing an alarm during autoregulation monitoring, in accordance with an embodiment.

FIGS. 6 and 7 are process flow diagrams of methods of providing an alarm(s) during autoregulation monitoring, in accordance with embodiments of the present disclosure. The methods include various steps represented by blocks. The methods may be performed as an automated procedure by a system, such as system 10. In particular, some or all of the steps of the methods may be implemented by the controller 16 (e.g., the processor 24 of the controller 16) of FIG. 1, for example, to monitor the patient's autoregulation and/or to take an appropriate action (e.g., output a visual or audible alarm, or the like). Although the flow charts illustrate steps in a certain sequence, it should be understood that the steps may be performed in any suitable order and certain steps may be carried out simultaneously, where appropriate. Additionally, steps of the methods may be combined with other methods and/or may incorporate other disclosed steps in any suitable manner. Further, certain steps or portions of the methods may be performed by separate devices. For example, a first portion of the method may be performed by the controller 16, while a second portion of the method may be performed by the sensor 14. In addition, insofar as steps of the methods are applied to received signals, it should be understood that the received signals may be raw signals or processed signals. That is, the methods may be applied to an output of the received signals.

FIG. 6 is a process flow diagram of a method 130 of providing an alarm(s) during autoregulation monitoring, in accordance with an embodiment. In step 132, the controller 16 may receive the blood pressure signal (e.g., arterial blood pressure signal). In some embodiments, the controller 16 may receive the blood pressure signal from the blood pressure sensor 12, as set forth above. In step 134, the controller 16 may receive the oxygen saturation signal (e.g., regional oxygen saturation signal). In some embodiments, the controller 16 may receive the oxygen saturation signal from the oxygen saturation sensor 14, as set forth above. As noted above, in some embodiments, the HVx, Mx, PRx, and/or gradients may be determined and utilized to monitor the patient's autoregulation and generate an appropriate alarm(s).

In step 136, the controller 16 may compare the blood pressure and/or the oxygen saturation to a respective predetermined range. In step 138, the controller 16 may generate a physiological parameter alarm if the blood pressure and/or the oxygen saturation are outside of the respective predetermined range. In step 140, the controller 16 may calculate a COx value based on the blood pressure signal and the oxygen saturation signal. In step 142, the controller 16 may determine whether the COx value indicates an impaired autoregulation status, and may provide an autoregulation alarm if the COx value indicates impaired autoregulation. As discussed above, in some embodiments, the controller 16 may provide the autoregulation alarm only if the COx value indicates impaired autoregulation for more than a predetermined period of time. Furthermore, in some embodiments, the autoregulation alarm may include multiple flags and/or alarms. For example, an autoregulation flag may be set or provided upon initial detection of trending and/or a correlation between the blood pressure signal and the oxygen saturation signal. At a later time, an autoregulation alarm may be provided upon determination of impaired autoregulation for more than the predetermined period of time.

FIG. 7 is a process flow diagram of a method 150 of providing an alarm(s) during autoregulation monitoring, in accordance with an embodiment. In step 152, the controller 16 may receive the blood pressure signal (e.g., arterial blood pressure signal). In some embodiments, the controller 16 may receive the blood pressure signal from the blood pressure sensor 12, as set forth above. In step 154, the controller 16 may receive the oxygen saturation signal (e.g., regional oxygen saturation signal). In some embodiments, the controller 16 may receive the oxygen saturation signal from the oxygen saturation sensor 14, as set forth above. As noted above, in some embodiments, the HVx, Mx, PRx, and/or gradients may be determined and utilized to monitor the patient's autoregulation and generate an appropriate alarm(s). In some embodiments, the controller 16 may be configured to provide an indication (e.g., via the output device 18) that the patient's blood pressure and/or oxygen saturation are within the respective range and/or an indication of intact autoregulation based on the COx value.

In step 156, the controller 16 may access and/or determine an LLA and/or a ULA. For example, the LLA and/or the ULA may have been previously determined for the patient and stored (e.g., in the memory device 26) for access by the controller 16. In some embodiments, the controller 16 may determine the LLA and/or the ULA based on COx values calculated across blood pressures over time during the monitoring session. In step 158, the controller 16 may determine whether the blood pressure is outside of an intermediate range (e.g., intact autoregulation range or blood pressure safe zone) defined between the LLA and/or the ULA. In some embodiments, if the patient's blood pressure is within the intermediate range, in step 160, the controller 16 may provide an indication of intact autoregulation. If the patient's blood pressure is outside of the intermediate range, in step 162, the controller 16 may calculate an integral over time of a difference between the blood pressure signal and the LLA and/or the ULA. For example, the controller 16 may calculate the integral over time of the difference between the blood pressure signal and the LLA if the blood pressure signal is below the LLA, and the controller 16 may calculate the integral over time of the difference between the blood pressure signal and the ULA if the blood pressure signal is above the ULA. In step 164, the controller 16 may compare the integral over time to a predetermined integral threshold. In step 166, the controller 16 may provide an autoregulation limit alarm if the integral over time exceeds the predetermined integral threshold.

The methods 130 and 150 may be combined in any suitable manner. For example, the method 130 may be carried out during one portion of a monitoring session (e.g., at the beginning of the monitoring session and/or prior to determination of the ULA and/or the LLA), and the method 150 may be carried out during another portion of the monitoring session (e.g., after determination of the ULA and/or the LLA). Additionally or alternatively, various steps of the methods 130 and 150 may be combined. For example, steps 136 and 138 may be included in the method 150 of FIG. 7. In such cases, the controller 16 may be configured to provide the physiological parameter alarm if the blood pressure and/or the oxygen saturation are outside of the respective predetermined range, and to provide the autoregulation limit alarm if the integral over time exceeds the predetermined integral threshold.

Figure 8:
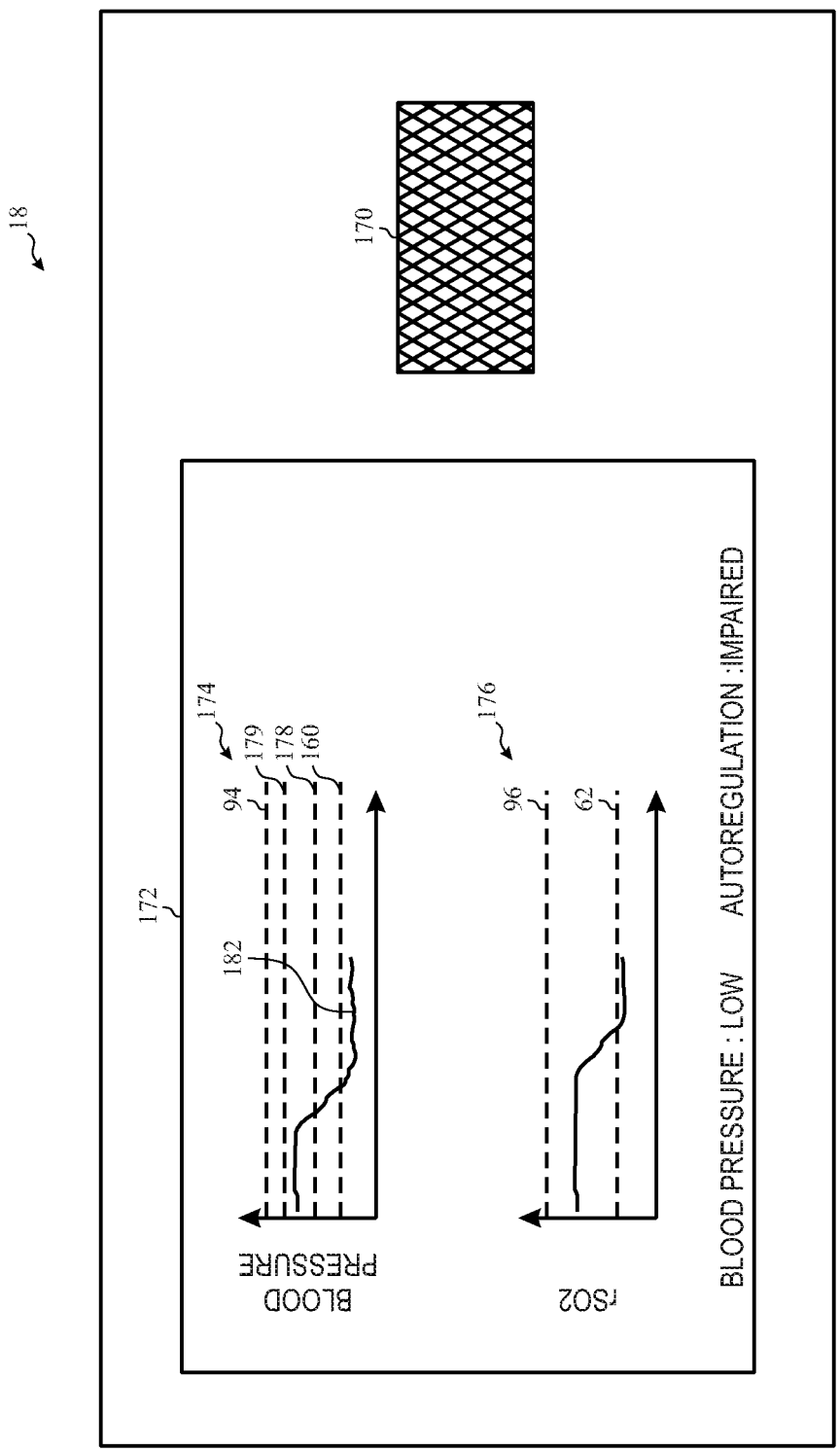
FIG. 8 is an example of an output device configured to provide an alarm indication related to the patient's autoregulation status.

FIG. 8 is an example of the output device 18 having a speaker 170 and a display 172 and configured to provide an alarm(s) related to the patient's autoregulation function. As shown, the display 172 is configured to display a graph 174 of blood pressure over time. In some embodiments, the display 172 is configured to display a graph 176 of oxygen saturation over time. As shown, the graphs 174, 176 includes or overlays a representation of respective predetermined thresholds. In the illustrated embodiment, an LLA 178 and an ULA 179 are also indicated on the graph 174. Thus, as the patient's blood pressure signal 182 (e.g., a current blood pressure signal) is obtained and plotted on the graph 174, the patient's current autoregulation state may be indicated and/or viewed by a clinician. Additionally, audible and/or visual alarm(s) may be provided when the patient's blood pressure and/or oxygen saturation falls outside of the respective thresholds 60, 62, 94, 96, 178, 179. In some embodiments, audible and/or visual alarm(s) may be provided in response to determination of impaired autoregulation status. For example, in the illustrated embodiment, a text message indicating low blood pressure and a text message indicating impaired autoregulation is provided on the display 172. In some embodiments, any of the various graphs or features of the graphs illustrated in FIGS. 2-5 may be provided via the display 172.

FIGS. 1-8 generally relate to systems and methods for generating various types of alarms, and FIGS. 9-12 generally relate to systems and methods for generating and analyzing an autoregulation profile. It should be appreciated that any of the features of the systems and methods disclosed herein may be utilized in combination with one another to facilitate autoregulation monitoring. For example, the autoregulation profile shown in FIG. 2 may be used to establish the blood pressure safe zone, the ULA and/or the LLA, which may then be used to generate an alarm via the steps of the method 130 of FIG. 6 and/or the steps of the method 150 of FIG. 7, for example.

With the foregoing in mind, in certain embodiments, a measure of autoregulation (e.g., COx, HVx, Mx, PRx, or gradients) may facilitate generation of an autoregulation profile of the patient. The autoregulation profile may include the autoregulation status or state across blood pressures, and may be schematically represented by the autoregulation state plotted on a vertical axis and blood pressure plotted on a horizontal axis. In certain embodiments, the patient's autoregulation profile may be represented as a vector (A) of autoregulation state indexed by blood pressure. Thus, the autoregulation state at a particular blood pressure, BP, is given by A(BP). In some embodiments, an intact autoregulation state may be represented as a positive value (e.g., positive autoregulation state value or vector value), and an impaired autoregulation state may be represented as a negative value (e.g., positive autoregulation state value or vector value). In certain embodiments, an absolute value of the autoregulation state value corresponds to a confidence level associated with the autoregulation state. For example, greater absolute values correspond to greater confidence levels, while lower absolute values correspond to lower confidence levels.

In operation, the controller 16 may obtain physiological signals, calculate the measure indicative of autoregulation (e.g., COx, HVx, Mx, PRx, or gradients), and determine an autoregulation state based on the measure. In some embodiments, the controller 16 may calculate and/or assign an autoregulation state value based on the measure and/or a confidence level associated with the measure. In some embodiments, the controller 16 may assign a positive value (e.g., +1) for an intact autoregulation state and a negative value (e.g., −1) for an impaired autoregulation state. For example, if the COx value indicates an intact autoregulation state (e.g., the COx value is between 0 and −1) at a particular blood pressure (e.g., blood pressure or blood pressure range), an autoregulation state value of +1 may be assigned to the particular blood pressure. In some embodiments, if the determined autoregulation state has a high confidence level (e.g., based on various factors or metrics, a confidence level over a predetermined threshold), an absolute value of the autoregulation state value may be relatively higher or increased, such as from +1 to +2. As the physiological signals are obtained and processed over time, the controller 16 may generate the autoregulation profile representative of the autoregulation state across blood pressures.

In turn, the autoregulation profile may facilitate identification of autoregulation zones indicative of a patient's blood pressure dependent autoregulation state. As noted above, a patient's autoregulation system may typically function well over a certain range of blood pressures. Accordingly, each patient typically exhibits at least three autoregulation zones:

a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired.

With the foregoing in mind, in some embodiments, the disclosed systems and methods may utilize the autoregulation profile to determine a patient-specific blood pressure safe zone (i.e., a blood pressure range associated with an intact autoregulation state or the intact autoregulation zone) by identifying a largest, continuous positive region of the autoregulation profile. In some embodiments, the disclosed systems and methods may determine a patient-specific blood pressure safe zone by identifying a positive peak of the autoregulation profile and identifying nearest blood pressures associated with impaired autoregulation. In some embodiments, the disclosed systems and methods may include techniques for removing anomalous autoregulation states from the autoregulation profile and/or discarding unreliable data.

In certain embodiments, the systems and methods may provide an indication (e.g., visual indication on a display) of the autoregulation profile and/or the blood pressure safe zone. In certain embodiments, the systems and methods may display other information, such as a target blood pressure (TBP), an upper limit of autoregulation (ULA) value, and/or a lower limit of autoregulation (LLA). The TBP may represent a blood pressure value or a range of blood pressure values at which the patient's autoregulation function is greatest and/or may be useful for clinical management of a patient's blood pressure. For example, the TBP may guide a healthcare provider's treatment of the patient (e.g., provide an indication of whether the healthcare provider should administer medication to lower the patient's blood pressure or to raise the patient's blood pressure to reach the TBP within the intact autoregulation zone). The TBP may be displayed in a variety of ways (e.g., point, number, vertical line, etc.). In certain embodiments, the systems and methods may indicate a distance of the patient's measured blood pressure from the TBP. As discussed above, the ULA and the LLA approximately define an upper and a lower blood pressure boundary, respectively, of the blood pressure safe zone within which autoregulation is generally intact and functions properly. Blood pressures approximately above the ULA and/or approximately below the LLA may be associated with impaired autoregulation function. The ULA and/or the LLA may be displayed in a variety of ways (e.g., point, number, vertical line, etc.). In certain embodiments, a blood pressure signal (i.e., a plot of blood pressure values over time) may overlay a graphical indicator of the blood pressure safe zone. In some embodiments, if the patient's current blood pressure falls outside of the blood pressure safe zone, the system may provide an alarm (e.g., audible or visual indication).

As noted above, the controller 16 may determine a COx value, which may be between −1 and 1, inclusive, where −1 represents total negative correlation, +1 represents total positive correlation, and 0 represents the absence of correlation between the blood pressure measurements and the oxygen saturation measurements. Thus, COx values between −1 and 0 may suggest that cerebral autoregulation is working properly (e.g., an intact autoregulation state), while COx values between 0 and 1 may suggest that the cerebral autoregulation is impaired (e.g., an impaired autoregulation state). In some cases, a predetermined threshold between 0 and 1 may be utilized to determine whether the patient's autoregulation is impaired. For example, in some embodiments, the controller 16 may be configured to determine that the patient's autoregulation is impaired (e.g., an impaired autoregulation state) when the COx value is greater than 0.1, 0.2, 0.3, 0.4, 0.5, 0.6, 0.7, 0.8, or 0.9. Accordingly, the controller 16 may be configured to determine the COx value and/or the patient's autoregulation state based on the linear correlation between the blood pressure measurements and oxygen saturation measurements obtained by the blood pressure sensor 12 and the oxygen saturation sensor 14, respectively.

In some embodiments, the controller 16 may convert the COx value to and/or represent the patient's autoregulation state as a value (e.g., autoregulation state value). For example, if the COx value indicates an intact autoregulation state (e.g., the COx value is between 0 and −1) at a particular blood pressure (e.g., blood pressure or blood pressure range), the controller 16 may assign a positive value (e.g., +1) to the particular blood pressure. However, if the COx value indicates an impaired autoregulation state (e.g., the COx value is between 0 and +1, or is greater than a predetermined threshold, such as 0.1, 0.2, 0.3, 0.4, 0.5, 0.6, 0.7, 0.8, or 0.9) at the particular blood pressure, the controller 16 may assign a negative value (e.g., −1) to the particular blood pressure. As discussed in more detail below, the controller 16 may calculate and/or adjust the autoregulation state value based on a confidence level associated with the measure. In some embodiments, the autoregulation state value may be updated over time as new data points are collected and/or the autoregulation profile may be generated based on the autoregulation state values across blood pressures.

Figure 9:
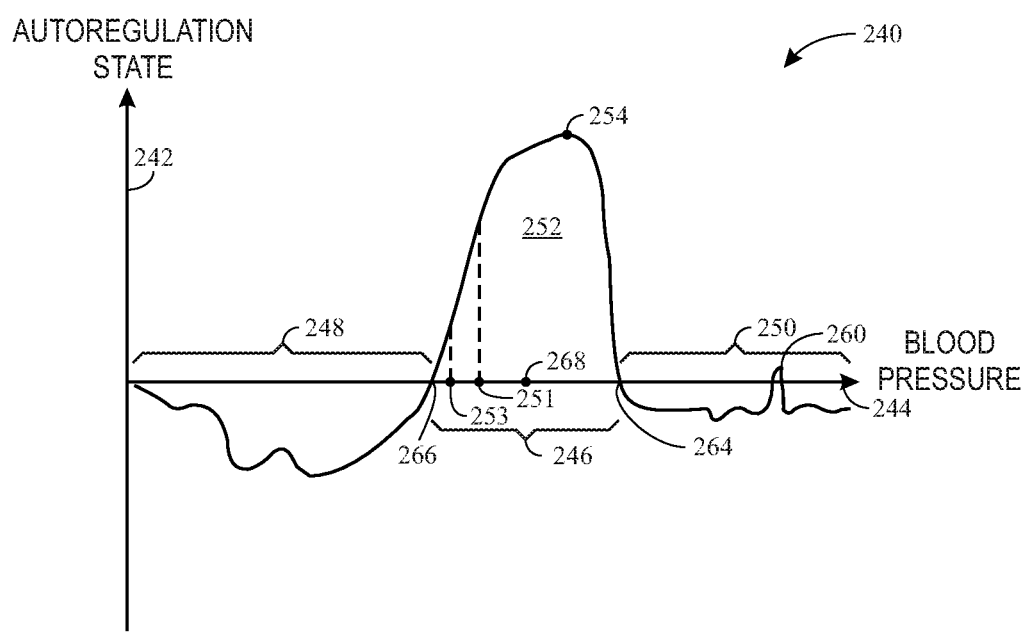
FIG. 9 is an example of a graph illustrating autoregulation state plotted against blood pressure.

With the foregoing in mind, FIG. 9 illustrates a schematic representation of a patient's autoregulation profile 240, in accordance with an embodiment of the present disclosure. As shown, the autoregulation profile 240 may be represented schematically with an autoregulation state 242 on a vertical axis and blood pressure 244 on a horizontal axis.

As noted above, an intact autoregulation state may be represented as a positive value (e.g., positive autoregulation state value), and an impaired autoregulation state may be represented as a negative value (e.g., positive autoregulation state value). In certain embodiments, an absolute value of the autoregulation state value corresponds to and/or is based on a confidence level associated with the autoregulation state. Accordingly, with reference to FIG. 9, a region 246 encompassing positive autoregulation state values corresponds to an intact autoregulation state (e.g., a blood pressure safe zone), and regions 248, 250 encompassing negative autoregulation state values correspond to impaired autoregulation states. Additionally, a confidence level that a first blood pressure 251 is within the blood pressure safe zone is greater than a confidence level that a second blood pressure 253 is within the blood pressure safe zone.

The confidence level associated with the autoregulation state 242 may be determined in any suitable manner. In some embodiments, the confidence level may vary based at least in part on a significance value (p value) related to the linear correlation between the blood pressure and the oxygen saturation. For example, if the p value is above a predetermined threshold (e.g., 0.01, 0.05, or the like), the controller 16 may determine that the corresponding portion of the COx signal is reliable and may assign an autoregulation state value having a relatively greater absolute value (e.g., as compared to when the p value is below the predetermined threshold).

Additionally or alternatively, the confidence level may vary based at least in part on prior data at the particular blood pressure. For example, the confidence level may vary based at least in part on a number of data points (e.g., COx values, gradient measures, etc.) at the particular blood pressure that agree (e.g., indicate the same autoregulation state, such as intact or impaired). For example, if multiple (e.g., more than approximately 2, 3, 4, 5, 10, 15, etc.) COx values at the particular blood pressure indicate an intact autoregulation state, then the controller 16 may assign an autoregulation state value having a relatively greater absolute value. However, if COx values at the particular blood pressure disagree (e.g., indicate different autoregulation states) or if a limited number of data points at the particular blood pressure are available (e.g., less than 2, 3, 4, 5, 10, or the like), then the controller 16 may assign an autoregulation state value having a relatively lower absolute value. Additionally or alternatively, the confidence level may vary based at least in part on the autoregulation state at neighboring blood pressures (e.g., higher and lower blood pressures). For example, if the COx value indicates the same autoregulation state as both higher and lower blood pressures, then the controller 16 may assign an autoregulation state value having a relatively greater absolute value. However, if the COx value indicates a different autoregulation state than both higher and lower blood pressures, then the controller 16 may assign an autoregulation state value having a relatively lower absolute value.

Additionally or alternatively, the confidence level may vary based at least in part on a signal quality metric (e.g., of the oxygen saturation and/or blood pressure signal). Any suitable signal quality indicator may be considered, including a signal measure indicative of a low light level; a signal measure indicative of an arterial pulse shape; a signal measure indicative of the high frequency signal component in the measured value; a signal measure indicative of a consistency of a pulse shape; a signal measure indicative of an arterial pulse amplitude; and a signal measure indicative of a period of an arterial pulse, for example. These various indicators provide an indirect assessment of the presence of known error sources in blood pressure or oxygen saturation signals, which include optical interference between the sensor and the tissue location, physical movement of the patient, and/or improper tissue-to-sensor positioning, for example. The value of the quality metric may then be compared to a quality metric threshold. For example, if the quality metric is above the quality metric threshold, the controller 16 may determine that the corresponding portion of the COx signal is reliable and may assign an autoregulation state value having a relatively greater absolute value (e.g., as compared to when the quality metric is below the quality metric threshold).

Additionally or alternatively, the confidence level may vary based at least in part on an absolute value of an index measure, such as a COx value. For example, if the COx value is greater than 0.8, then the controller 16 may assign a negative autoregulation state value having a relatively greater absolute value. However, if COx value is between 0 and 0.8, then the controller 16 may assign a negative autoregulation state value having a relatively lower absolute value. Similarly, the confidence level may vary with an absolute value of the gradients (e.g., the oxygen saturation gradient or the blood pressure gradient when utilizing gradient techniques) and the autoregulation state value may be adjusted based on the absolute value of the gradients. For example, as the absolute values of the gradients increase, the absolute value of the autoregulation state value may increase. Thus, in certain embodiments, the controller 16 may calculate and/or adjust the autoregulation state value based at least in part the p value, prior data points at the particular blood pressure and/or neighboring blood pressures, signal quality metric(s), absolute values of the index measure or gradients, or any other suitable indicator of the confidence level associated with the autoregulation state.

The autoregulation profile 240 (e.g., the patient's autoregulation state 242 across blood pressure 244) may be utilized to determine autoregulation zones indicative of a patient's blood pressure dependent autoregulation state. For example, in some embodiments, the controller 16 may be configured to determine the patient-specific blood pressure safe zone 246 (i.e., the blood pressure range associated with an intact autoregulation state or the intact autoregulation zone) by identifying a largest, continuous positive area 252 of the autoregulation profile 240. In some embodiments, the area 252 may be identified by determining a largest blood pressure range (e.g., a largest blood pressure range associated with a positive autoregulation state 242). In some embodiments, the area 252 may be identified by integrating autoregulation state 242 with blood pressure 244. In some embodiments, the controller 16 may be configured to identify a ULA 264 and LLA 266 at the boundaries of the area 252 (e.g., the lowest blood pressure in the area 252 may be denoted as the LLA and the highest blood pressure in the area 252 may be denoted as the ULA). In some embodiments, the controller 16 may be configured to determine the TBP. For example, in some embodiments, the controller 16 may calculate the TBP at a midpoint 268 between the ULA 264 and the LLA 266 (e.g., (ULA+LLA)/2), or the controller 16 may calculate the TBP as the blood pressure associated with a positive peak 254 within the area 252 (e.g., corresponding to an intact autoregulation state with the highest confidence level). In some embodiments, the TBP may be a blood pressure or a range of blood pressures (e.g., a range encompassing and/or centered about the blood pressure associated with the midpoint or the peak 254, such as within approximately 1, 2, 3, 4, 5, or 10 mmHg or within about 1, 2, 3, 4, 5, or 10 percent of the blood pressure associated with the midpoint or the peak 254).

In some embodiments, the controller 16 may determine the patient-specific blood pressure safe zone 246 by identifying the peak 254 of the autoregulation profile 240 and identifying nearest blood pressures associated with impaired autoregulation. For example, with reference to FIG. 9, after the peak 254 is identified, the ULA 264 may be identified at the nearest impaired blood pressure 256 above the blood pressure associated with the peak 254 and the LLA 266 may be identified at the nearest impaired blood pressure 258 below the blood pressure associated with the peak 254. In some such embodiments, the TBP may be a blood pressure or a range of blood pressures (e.g., a range encompassing and/or centered about the blood pressure associated with the midpoint or the peak 254, such as within approximately 1, 2, 3, 4, 5, or 10 mmHg or within about 1, 2, 3, 4, 5, or 10 percent of the blood pressure associated with the midpoint or the peak 254).

In some embodiments, the controller 16 may be configured to remove anomalous data (e.g., anomalous autoregulation states) from the autoregulation profile 240 and/or discard unreliable data. For example, with reference to FIG. 9, an anomalous region 260 (e.g., a region in which the autoregulation state does not agree with the autoregulation states at both higher and lower blood pressures) may be removed, discarded, or ignored when determining the ULA, the LLA, and/or the TBP and/or prior to displaying an indication of the patient's autoregulation profile or related information. In some embodiments, a smoothing kernel (e.g., a Gaussian smoothing filter, mean filter, or the like) may be applied to filter out anomalous regions, as discussed in more detail below.

In some embodiments, the controller 16 may be configured to discard autoregulation states 242 having autoregulation state values below a predetermined threshold. Such autoregulation states 242 may indicate that insufficient number of data points have been obtained at the particular blood pressure and/or that the autoregulation state 242 at the particular blood pressure has an insufficient confidence level. For example, in some embodiments, the controller 16 may not consider and/or output data indicative of the autoregulation state at a particular blood pressure until at least 2, 3, 4, 5 or more COx values (e.g., COx values having sufficient confidence levels) are calculated for the particular blood pressure. In some embodiments, the controller 16 may not consider and/or output data indicative of the autoregulation state at a particular blood pressure until the autoregulation state value at the particular blood pressure exceeds a predetermined threshold. In some embodiments, this thresholding step may be ignored or bypassed if autoregulation states at neighboring blood pressures (e.g., above and below the particular blood pressure) agree. Identifying blood pressures associated with the various autoregulation zones may, in turn, facilitate efficient and/or reliable determination of the patient's current autoregulation status during patient monitoring.

With reference to FIG. 1, it should be appreciated that the processor 24 may be used to execute software, such as software for carrying out any of the techniques disclosed herein, such as processing the blood pressure signals and/or oxygen saturation signals, determining a measure of autoregulation (e.g., index value or gradients), determining the autoregulation state, calculating and/or assigning the autoregulation state value, determining the TBP, identifying autoregulation zones, identifying the LLA and/or the ULA, causing display of information related to the autoregulation profile, the blood pressure safe zone, and/or the current autoregulation status on a display, and so forth. Furthermore, the memory device 26 may store processor-executable instructions (e.g., firmware or software) for the processor 24 to execute, such as instructions for processing the blood pressure signals and/or oxygen saturation signals, determining a measure of autoregulation (e.g., index value or gradients), determining the autoregulation state, calculating and/ or assigning the autoregulation state value, determining the TBP, identifying autoregulation zones, identifying the LLA and/or the ULA, causing display of information related to the autoregulation profile, the blood pressure safe zone, and/or the current autoregulation status on a display, and so forth.

In some embodiments, the storage device(s) may store data (e.g., the blood pressure signal, the oxygen saturation signal, the index value, the blood pressure safe zone, the autoregulation profile, the TBP, etc.), instructions (e.g., software or firmware for processing the blood pressure signals and/or oxygen saturation signals, determining a measure of autoregulation (e.g., index value or gradients), determining the autoregulation state, calculating and/or assigning the autoregulation state value, determining the TBP, identifying autoregulation zones, identifying the LLA and/or the ULA, causing display of information related to the autoregulation profile, the blood pressure safe zone, and/or the current autoregulation status on a display, and so forth), predetermined thresholds, and any other suitable data.

As shown in FIG. 1, the system 10 includes the output device 18. In some embodiments, the controller 16 may be configured to provide signals indicative of the autoregulation profile, the blood pressure safe zone, the TBP, the LLA, the ULA, the current blood pressure, the distance of current blood pressure from the TBP, and/or the patient's autoregulation status (e.g., current blood pressure relative to the blood pressure safe zone) to the output device 18. In some embodiments, the controller 16 may be configured to generate an alarm signal indicative of the patient's autoregulation status and to provide the alarm signal to the output device 18. For example, in certain embodiments, if the current blood pressure of the patient falls outside of the blood pressure safe zone, the controller 16 may provide an alarm (e.g., audible or visual indication) via the output device 18. In certain embodiments, the alarm may differentiate between a blood pressure below the blood pressure safe zone and a blood pressure above the blood pressure safe zone. This differentiation may be provided via two different beeps (one representative of blood pressure below the blood pressure safe zone and one representative of blood pressure above the blood pressure safe zone) provided via the output device 18 (e.g., speaker). The beeps may differ in tones, durations, volume, tunes, or other types of audible features.

As noted above, the output device 18 may include any device configured to receive signals (e.g., signals indicative of the autoregulation profile, the blood pressure safe zone, the TBP, the LLA, the ULA, the current blood pressure, the distance of current blood pressure from the TBP, the patient's autoregulation status, the alarm signal, or the like) from the controller 16 and visually and/or audibly output information indicative of the patient's autoregulation status (e.g., the autoregulation profile, the Blood pressure safe zone, the TBP, the LLA, the ULA, the current blood pressure, the distance of current blood pressure from the TBP, the patient's autoregulation status, the alarm signal, a message, or the like). For instance, the output device 18 may include a display configured to provide a visual representation of the autoregulation profile, the blood pressure signal, the blood pressure safe zone, the TBP, the LLA, the ULA, the current blood pressure, the distance between the current blood pressure and the TBP, the alarm signal, or the like, as determined by the controller 16. In some embodiments, the controller 16 may instruct the output device 18 may be configured to display a graph of the autoregulation profile in the format shown in of FIG. 9. Additionally or alternatively, the output device 18 may include an audio device configured to provide sounds (e.g., spoken message, beeps, or the like) indicative of the patient's autoregulation profile, the BP signal, the blood pressure safe zone, the TBP, the LLA, the ULA, the current blood pressure, the distance between the current blood pressure and the TBP, the alarm signal, or the like.

Figure 10:
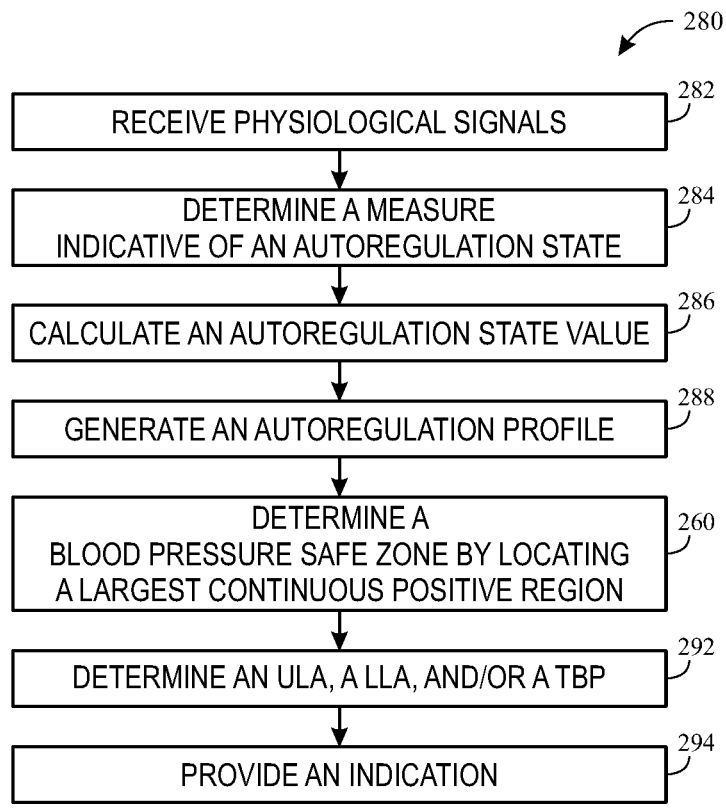
FIG. 10 is a process flow diagram of a method of monitoring autoregulation that includes identifying blood pressure zones, in accordance with an embodiment.
Figure 11:
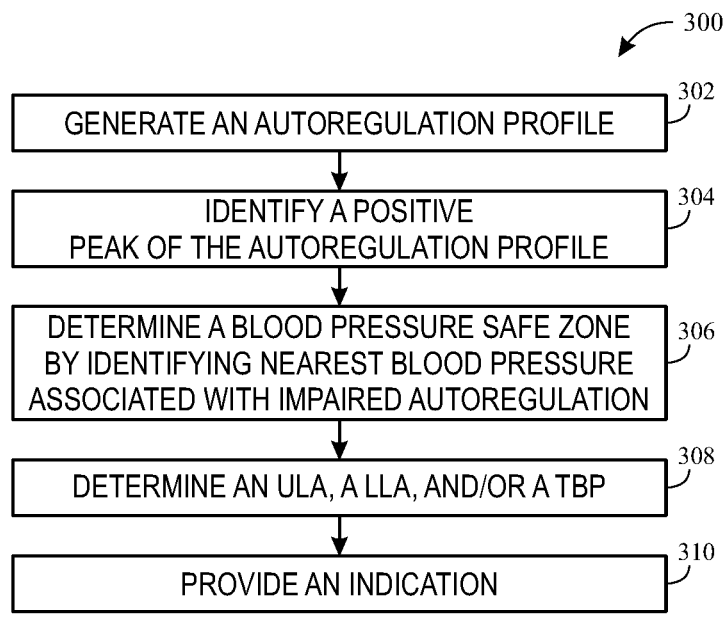
FIG. 11 is a process flow diagram of another method of monitoring autoregulation that includes identifying blood pressure zones, in accordance with an embodiment.

FIGS. 10 and 11 are process flow diagrams of methods of monitoring autoregulation, in accordance with embodiments of the present disclosure. The methods include various steps represented by blocks. The methods may be performed as an automated procedure by a system, such as system 10. In particular, some or all of the steps of the methods may be implemented by the controller 16 (e.g., the processor 24 of the controller 16) of FIG. 1, for example, to monitor the patient's autoregulation and/or to take an appropriate action (e.g., output a visual or audible indication related to autoregulation, or the like). Although the flow charts illustrate steps in a certain sequence, it should be understood that the steps may be performed in any suitable order and certain steps may be carried out simultaneously, where appropriate. Additionally, steps of the methods may be combined with other methods and/or may incorporate other disclosed steps in any suitable manner (e.g., the steps of the method 130 of FIG. 6 and/or the steps of the method 150 of FIG. 7). Further, certain steps or portions of the methods may be performed by separate devices. For example, a first portion of the method may be performed by the controller 16, while a second portion of the method may be performed by the sensor 14. In addition, insofar as steps of the methods are applied to received signals, it should be understood that the received signals may be raw signals or processed signals. That is, the methods may be applied to an output of the received signals.

As shown in the method 280 of FIG. 10, in step 282, the controller 16 receives physiological signals from a patient. For example, the controller 16 may receive a blood pressure signal from the blood pressure sensor 12 and an oxygen saturation signal from the oxygen saturation sensor 14. In step 284, the controller 16 may determine a measure indicative of an autoregulation state, such as a COx value. As noted above, in some embodiments, the HVx, Mx, PRx, and/or gradients may be determined and utilized to monitor the patient's autoregulation. In step 286, the controller 16 may calculate and/or assign an autoregulation state value based on the measure and/or a confidence level associated with the measure. For example, in some embodiments, the controller 16 may assign a positive value (e.g., +1) for an intact autoregulation state and a negative value (e.g., −1) for an impaired autoregulation state. In certain embodiments, the controller 16 may calculate and/or adjust the autoregulation state value based at least in part the p value, prior data points at the particular blood pressure and/or neighboring blood pressures, signal quality metric(s), absolute values of the index measure or gradients, or any other suitable indicator of the confidence level associated with the autoregulation state. In step 288, the controller 16 may generate and/or update an autoregulation profile (e.g., the autoregulation profile 240) for a patient based on the calculated autoregulation state value. As discussed above, the autoregulation profile may be indicative of the autoregulation state across blood pressures.

In step 290, the controller 16 may determine a patient-specific blood pressure safe zone (e.g., region 246) by identifying a largest, continuous positive area (e.g., area 252) of the autoregulation profile. As discussed above, the area may be identified based on a largest blood pressure range and/or by integrating autoregulation state with blood pressure. In step 292, the controller 16 may determine the ULA, the LLA, and/or the TBP based on the blood pressure safe zone determined in step 290. In some embodiments, the controller 16 may be configured to identify the ULA (e.g., the ULA 264) and the LLA (e.g., the LLA 266) at the boundaries of the area (e.g., the lowest blood pressure in the area 252 may be denoted as the LLA and the highest blood pressure in the area 252 may be denoted as the ULA). In some embodiments, the controller 16 may calculate the TBP at the midpoint (e.g., the midpoint 268) between the ULA and the LLA, or the controller 16 may calculate the TBP at a positive peak within the area (e.g., the positive peak 254 within the area 252). In step 294, the controller 16 may instruct the output device 18 to provide an indication related to the patient's autoregulation (e.g., the autoregulation profile, the blood pressure safe zone, the TBP, the LLA, the ULA, and/or an alarm).

FIG. 11 is a process flow diagram of a method 300 of monitoring autoregulation, in accordance with an embodiment. As shown in FIG. 11, in step 302, the controller 16 may generate an autoregulation profile (e.g., the autoregulation profile 240) for a patient. As discussed above, the autoregulation profile may be generated by the controller 16 after carrying out the steps 282-288 of the method 280 of FIG. 3, and the autoregulation profile may be indicative of the autoregulation state across blood pressures.

In step 304, the controller 16 may identify a positive peak (e.g., the positive peak 254) of the autoregulation profile. In some embodiments, the controller 16 may implement a peak finding algorithm to identify the positive peak. In step 306, the controller 16 may determine a patient-specific blood pressure safe zone (e.g., region 246) by identifying blood pressures associated with impaired autoregulation that are nearest the blood pressure associated with the positive peak. For example, with reference to FIG. 9, after the positive peak 254 is identified, the boundaries of the blood pressure safe zone 246 may be identified at the nearest impaired blood pressure 256 above the blood pressure associated with the peak 254 and the at the nearest impaired blood pressure 258 below the blood pressure associated with the peak 254. In step 308, the controller 16 may determine the ULA, the LLA, and/or the TBP based on the blood pressure safe zone determined in step 306. In particular, the boundaries identified in step 106 may be designated as the ULA (e.g., the ULA 264) and the LLA (e.g., the LLA 266). In some embodiments, the controller 16 may calculate the TBP at the midpoint (e.g., the midpoint 268) between the ULA and the LLA, or the controller 16 may calculate the TBP at the positive peak. In step 310, the controller 16 may instruct the output device 18 to provide an indication related to the patient's autoregulation (e.g., the autoregulation profile, the blood pressure safe zone, the TBP, the LLA, the ULA, and/or an alarm).

Figure 12:
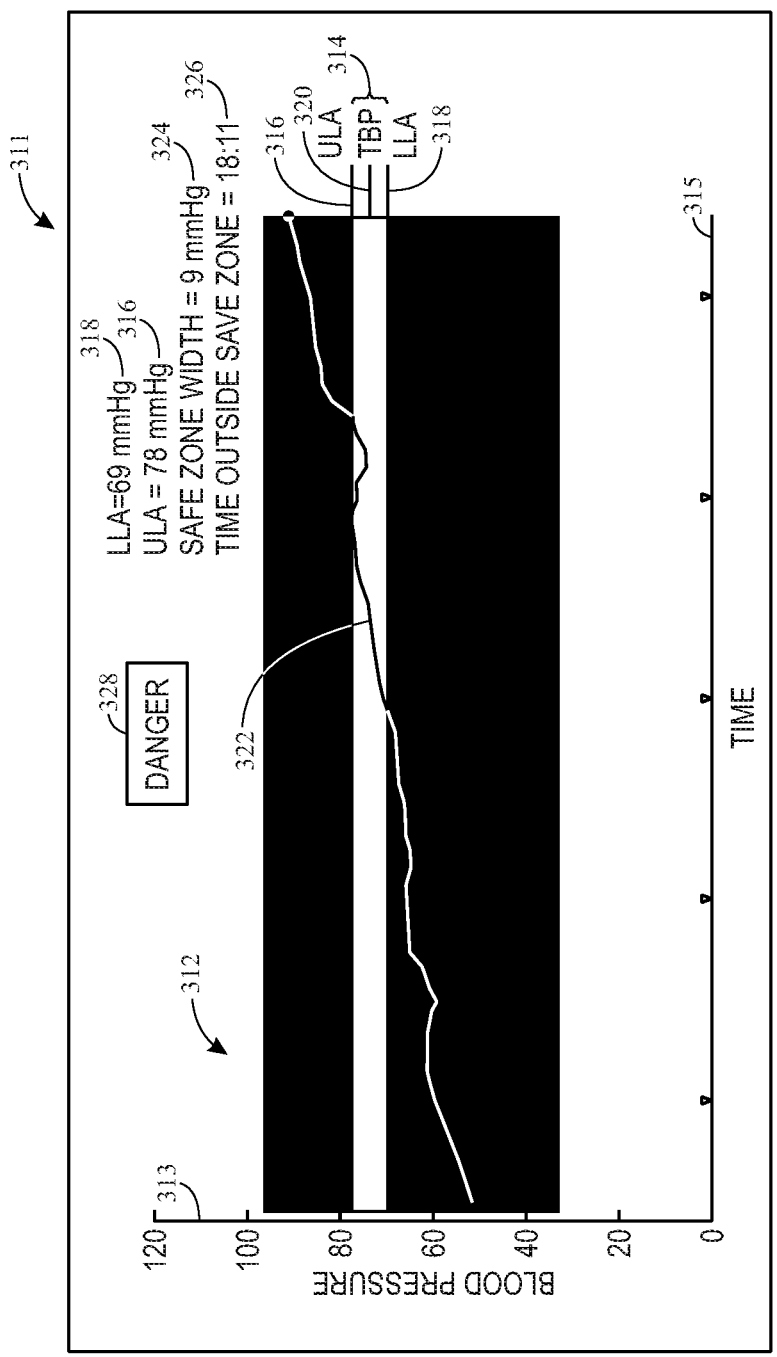
FIG. 12 is an example of a display configured to display information related to the patient's autoregulation status.

FIG. 12 is an example of a display 311 of an autoregulation status of a patient (e.g., displayed on the output device 18). As shown, a graph 312 includes blood pressure plotted on the vertical axis 313 and time plotted on the horizontal axis 315. As shown, the graph 312 includes or overlays a representation of the patient's autoregulation profile (e.g., the autoregulation profile 240). In the illustrated embodiment, a blood pressure safe zone 314, a ULA 316, a LLA 318, and/or a TBP 320 are indicated on the display 310. In some embodiments, the ULA 316, the LLA 318, and/or the TBP 320 may be indicated with numerical values and/or be labeled on the graph 312. Thus, as the patient's blood pressure signal 322 (e.g., a current blood pressure signal) is obtained and plotted on the graph 312 (e.g., overlays the representation of the patient's autoregulation profile), the patient's current autoregulation state may be indicated and/or viewed by a clinician.

In some embodiments, a width of the blood pressure safe zone 324 and/or a time spent outside of the blood pressure safe zone 326 may be provided. In some embodiments, an indication of the patient's current autoregulation status (e.g., intact or impaired) may be provided via a text message 328. In some embodiments, a color indicator on the display 310 may indicate the patient's current autoregulation state. In some embodiments, the color indicator may be a background color of the display 310. For example, in some embodiments, a first color (e.g., red) may indicate an impaired autoregulation state, a second color (e.g., green) may indicate an intact autoregulation state, a third color (e.g., grey) may indicate insufficient data regarding the autoregulation state at the patient's current blood pressure (e.g., an insufficient number of data points and/or low confidence in the data points), and/or a fourth color (e.g., black) may indicate that no data regarding the autoregulation state at the patient's current blood pressure exists. In some embodiments, a shade and/or a brightness of the colors may vary based on a confidence level associated with the indicated current autoregulation state.

Various other indications may be provided via the display 310. For example, in some embodiments, an oxygen saturation signal (e.g., rSO2 signal) may be provided on the display 310. In some embodiments, standard or typical blood pressure alarm limits 318 (e.g., maximum or minimum blood pressures) may be displayed. In some embodiments, the controller 16 and/or the display 310 may not provide autoregulation information outside of the standard blood pressure alarm limits. In some embodiments, the controller 16 may enable a clinician to modify the time shown on the display 310, thereby modifying an amount of data and/or history shown on the display 310.

In some embodiments, smoothing (e.g., a Gaussian smoothing filter, mean filter, or the like) may be applied to the autoregulation profile prior to presentation on the display 310. For example, a Gaussian smoothing filter may be applied across blood pressures to remove anomalous data, thereby providing a more reliable indication of the patient's autoregulation profile. In some embodiments, smoothed values may be utilized for display of the patient's autoregulation profile, while the original values (e.g., prior to the application of the smoothing filter) are utilized to determine the patient's current autoregulation status. In some embodiments, additional smoothing may be applied along the horizontal axis (i.e., time), and thus, the graph 312 may be smoothed via a 2D smoothing filter (e.g., 2D Gaussian smoothing filter, a 2D mean filter, or the like). In some embodiments, additional processing may include renormalizing reported autoregulation states by an amount of time spent at each blood pressure, which may enable a more direct comparison between blood pressures that are rarely visited and those blood pressures at which a lot of data points are collected.

It should be appreciated that some or all of the features shown or disclosed with respect to the display 172 of FIG. 8 and some or all of the features shown or disclosed with respect to the display 310 of FIG. 12 may be combined in any suitable manner. Furthermore, it should be appreciated that any of the various features of the systems and methods disclosed herein may be utilized together. For example, the features of the autoregulation profile 240 of FIG. 2 and some or all of the steps of the methods 280 and 300 of FIGS. 10 and 11, respectively, may be combined or utilized with the various alarms disclosed with reference to FIGS. 1-8. For example, in some embodiments, the blood pressure zones, ULA 264, the LLA 266 and/or other features identified based on the autoregulation profile 240 of FIG. 9 may be utilized to generate the autoregulation limit alarm, such as when the integral over time of the difference between the blood pressure and the ULA 264 or the LLA 266 exceeds the predetermined integral threshold. For example, in some embodiments, the features identified based on the autoregulation profile 240 may be utilized to generate the autoregulation limit alarm, which may be used in combination with a physiological parameter alarm if the blood pressure and/or the oxygen saturation are outside of the respective predetermined range.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A monitor configured to monitor autoregulation, the monitor comprising:
   a memory encoding one or more processor-executable instructions; and
   one or more processors configured to access and execute the one or more processor-executable instructions encoded by the memory, wherein the one or more processor-executable instructions, when executed cause the one or more processors to:
      receive one or more physiological signals from a patient, wherein the one or more physiological signals comprise a first physiological signal indicating a blood pressure of the patient at a given time;
      determine a set of blood pressure values based on the first physiological signal over a period of time;
      determine a set of correlation index values indicative of an autoregulation state of the patient based on the one or more physiological signals, wherein each correlation index value of the set of correlation index values is associated with a respective blood pressure value of the set of blood pressure values;
      generate an autoregulation profile of the patient based on the set of correlation index values, wherein the autoregulation profile comprises autoregulation state values assigned to corresponding blood pressure values of the set of blood pressure values, and wherein the autoregulation profile can be represented by the autoregulation state values plotted on a vertical axis and blood pressure values plotted on a horizontal axis; and
      identify a blood pressure safe zone of the autoregulation profile by at least:
         identifying a largest continuous positive region of the autoregulation profile; and
         designating the largest continuous positive region as the blood pressure safe zone.

2. The monitor of claim 1, wherein the one or more processor-executable instructions that cause the one or more processors to identify the largest continuous positive region comprise instructions that cause the one or more processors to integrate the autoregulation state values of the autoregulation profile as a function of blood pressure to identify a region associated with a largest area under the autoregulation profile as the largest continuous positive region.

3. The monitor of claim 1, wherein the one or more processor-executable instructions that cause the one or more processors to identify the largest continuous positive region comprise instructions that cause the one or more processors to locate a largest blood pressure range corresponding to positive autoregulation state values.

4. The monitor of claim 1, wherein the one or more processor-executable instructions that cause the one or more processors to identify the largest continuous positive region comprise instructions that cause the one or more processors to designate an upper limit of autoregulation (ULA) and a lower limit of autoregulation (LLA) at boundaries of the largest continuous positive region,
wherein the ULA is associated with a first blood pressure value of the set of blood pressure values, and
wherein the LLA is associated with a second blood pressure value of the set of blood pressure values.

5. The monitor of claim 4, wherein the memory further encodes one or more processor-executable instructions that, when executed, cause the one or more processors to:
identify a midpoint between the ULA and the LLA; and
designate a target blood pressure value of the set of blood pressure values encompassing the midpoint.

6. The monitor of claim 1, wherein the memory further encodes one or more processor-executable instructions that, when executed, cause the one or more processors to:
identify a maximum autoregulation state value of the autoregulation profile; and
designate, as at least one target blood pressure value of the set of blood pressure values, a blood pressure value or values selected from a group consisting of: a blood pressure value corresponding to the maximum autoregulation state value; and a range of blood pressures values that encompasses a blood pressure value corresponding to the maximum autoregulation state value.

7. The monitor of claim 1, wherein the memory further encodes one or more processor-executable instructions that, when executed, cause the one or more processors to:
determine a confidence level associated with at least one correlation index value of the set of correlation index values; and
calculate the autoregulation state values based on the confidence level associated with the at least one correlation index value of the set of correlation index values.

8. The monitor of claim 1, wherein the memory further encodes one or more processor-executable instructions that, when executed, cause the one or more processors to:
determine that an autoregulation state value from the autoregulation profile is below a threshold value; and
discard an autoregulation state value from the autoregulation profile if the respective autoregulation state value is below the threshold value.

9. The monitor of claim 1, wherein the set of correlation index values includes one of a cerebral oximetry index, a hemoglobin volume index, a mean velocity index, a pressure reactivity index, or a gradient measure.

10. The monitor of claim 1, wherein the memory further encodes one or more processor-executable instructions that, when executed, cause the one or more processors to provide a signal to a display or other output device to provide an audible or visual indication that a blood pressure value of the set of blood pressure values is outside the blood pressure safe zone.

11. The monitor of claim 1, wherein the memory further encodes one or more processor-executable instructions that, when executed, cause the one or more processors to generate an alarm in response to a blood pressure value of the set of blood pressure values being outside the blood pressure safe zone for more than a predetermined period of time.

12. The monitor of claim 1, wherein the memory further encodes one or more processor-executable instructions that, when executed, cause the one or more processors to:
designate an autoregulation limit at a boundary of the blood pressure safe zone, wherein the autoregulation limit is associated with a blood pressure value of the set of blood pressure values;
determine an integral over time of a difference between the set of blood pressure values and the autoregulation limit; and
generate an alarm indicative of an impaired autoregulation state in response to the integral over time exceeding a predetermined integral threshold.

13. The monitor of claim 12, wherein the memory further encodes one or more processor-executable instructions that, when executed, cause the one or more processors to generate an alarm in response to a blood pressure value of the set of blood pressure values falling outside of a respective predetermined blood pressure range.

14. A non-transitory computer-readable medium having computer executable code stored thereon, the computer executable code comprising instructions to:
receive one or more physiological signals from a patient, wherein the one or more physiological signals comprise a first physiological signal indicating a blood pressure of the patient;
determine a set of blood pressure values based on the first physiological signal;
determine a set of correlation index values indicative of an autoregulation state of the patient based on the one or more physiological signals, wherein each correlation index value of the set of correlation index values is associated with a respective blood pressure value of the set of blood pressure values;
generate an autoregulation profile of the patient based on the set of correlation index values, wherein the autoregulation profile comprises autoregulation state values assigned to corresponding blood pressure values, and wherein the autoregulation profile can be represented by the autoregulation state values plotted on a vertical axis and blood pressure values plotted on a horizontal axis;
identify a largest continuous positive region of the autoregulation profile; and
determine a blood pressure safe zone corresponding to the largest continuous positive region.

15. The non-transitory computer-readable medium of claim 14, wherein the instructions to identify the largest continuous positive region comprise instructions for integrating the autoregulation state values of the autoregulation profile as a function of blood pressure to identify a region associated with a largest area under the autoregulation profile as the largest continuous positive region.

16. The non-transitory computer-readable medium of claim 14, wherein the instructions to identify the largest continuous positive region comprise instructions for locating a largest blood pressure range in which all autoregulation state values in the largest blood pressure range are greater than a threshold level.

17. The non-transitory computer-readable medium of claim 14, wherein the instructions to generate the autoregulation profile of the patient comprise instructions for:
calculating the autoregulation state values based on the set of correlation index values by at least calculating a first autoregulation state value based on one or more correlation index values associated with a first blood pressure value of the set of blood pressure values; and
assigning each autoregulation state value to a corresponding blood pressure value of the set of blood pressure values by at least assigning the first autoregulation state value to the first blood pressure value.

18. A method for monitoring autoregulation, the method comprising:
determining, by one or more processors executing one or more instructions encoded on a memory, a set of blood pressure values based on a first physiological signal indicating a blood pressure of a patient;
determining, by the one or more processors, a set of correlation index values indicative of an autoregulation state of the patient based on one or more physiological signals including the first physiological signal, wherein each correlation index value of the set of correlation index values is associated with a respective blood pressure value of the set of blood pressure values;
generating, by the one or more processors, an autoregulation profile of the patient based on the set of correlation index values, wherein the autoregulation profile comprises autoregulation state values assigned to corresponding blood pressure values, and wherein the autoregulation profile can be represented by the autoregulation state values plotted on a vertical axis and blood pressure values plotted on a horizontal axis; and
identifying, by the one or more processors, a blood pressure safe zone of the autoregulation profile by at least:
identifying a largest continuous positive region of the autoregulation profile; and
designating the largest continuous positive region as the blood pressure safe zone.

19. A monitor configured to monitor autoregulation, the monitor comprising:
a memory encoding one or more processor-executable instructions; and
one or more processors configured to access and execute the one or more processor-executable instructions encoded by the memory, wherein the one or more processor-executable instructions, when executed cause the one or more processors to:
receive one or more physiological signals from a patient, wherein the one or more physiological signals comprise a first physiological signal indicating a blood pressure of the patient;
determine a set of blood pressure values based on the first physiological signal;
determine a set of correlation index values indicative of an autoregulation state of the patient based on the one or more physiological signals, wherein each correlation index value of the set of correlation index values is associated with a respective blood pressure value of the set of blood pressure values;
generate an autoregulation profile of the patient based on the set of correlation index values, wherein the autoregulation profile comprises autoregulation state values assigned to corresponding blood pressure value of the set of blood pressure values;
identify a blood pressure safe zone of the autoregulation profile;
designate an autoregulation limit as being defined by a blood pressure value at a boundary of the blood pressure safe zone;
determine an integral over time of a difference between the set of blood pressure values and the autoregulation limit; and
generate an alarm indicative of an impaired autoregulation state in response to the integral over time exceeding a predetermined integral threshold.

\* \* \* \* \*